United States Patent
Chuah et al.

(10) Patent No.: US 9,617,548 B2
(45) Date of Patent: Apr. 11, 2017

(54) LIVER-SPECIFIC NUCLEIC ACID REGULATORY ELEMENTS AND METHODS AND USE THEREOF

(75) Inventors: Marinee Chuah, Lovenjoel (BE); Thierry Vandendriessche, Lovenjoel (BE); Pieter De Bleser, Buggenhout (BE)

(73) Assignees: VIB VZW, Ghent (BE); Life Sciences Research Partners VZW, Leuven (BE); Universiteit Gent, Ghent (BE)

( * ) Notice: Subject to any disclaimer, the term of this patent is extended or adjusted under 35 U.S.C. 154(b) by 413 days.

(21) Appl. No.: 12/736,584

(22) PCT Filed: Apr. 21, 2009

(86) PCT No.: PCT/EP2009/054724
§ 371 (c)(1),
(2), (4) Date: Apr. 8, 2011

(87) PCT Pub. No.: WO2009/130208
PCT Pub. Date: Oct. 29, 2009

(65) Prior Publication Data
US 2011/0184049 A1    Jul. 28, 2011

Related U.S. Application Data

(60) Provisional application No. 61/125,181, filed on Apr. 22, 2008.

(51) Int. Cl.
*C07H 21/04* (2006.01)
*C12N 15/63* (2006.01)
*C12N 15/52* (2006.01)
*A61K 38/48* (2006.01)
*C07K 14/81* (2006.01)
*C12N 15/85* (2006.01)
*A61K 48/00* (2006.01)

(52) U.S. Cl.
CPC .......... *C12N 15/63* (2013.01); *A61K 38/4846* (2013.01); *C07K 14/8121* (2013.01); *C12N 15/52* (2013.01); *C12N 15/85* (2013.01); *A61K 48/00* (2013.01); *C12N 2799/025* (2013.01); *C12N 2799/027* (2013.01); *C12N 2830/008* (2013.01); *C12N 2830/15* (2013.01); *C12N 2830/85* (2013.01)

(58) Field of Classification Search
CPC ................................ C12N 15/63; C12N 15/52
See application file for complete search history.

(56) References Cited

U.S. PATENT DOCUMENTS

| | | | | |
|---|---|---|---|---|
| 5,824,837 A | * | 10/1998 | Chen et al. | 800/3 |
| 6,808,905 B2 | * | 10/2004 | McArthur et al. | 435/91.4 |
| 6,812,339 B1 | * | 11/2004 | Venter et al. | 536/24.31 |
| 7,351,813 B2 | * | 4/2008 | Miao et al. | 536/23.2 |
| 7,651,840 B2 | * | 1/2010 | Li et al. | 435/6.11 |
| 2003/0215858 A1 | * | 11/2003 | Templeton | 435/6 |
| 2005/0272054 A1 | * | 12/2005 | Cargill et al. | 435/6 |
| 2006/0189561 A1 | | 8/2006 | Roelvink | |

FOREIGN PATENT DOCUMENTS

| | | |
|---|---|---|
| WO | WO 95/11308 | 4/1995 |
| WO | WO 01/98482 | 12/2001 |
| WO | WO 2009/130208 A1 | 10/2009 |

OTHER PUBLICATIONS

Rollini et al. Nuc Acid Res 27(19):3779-3791, 1999.*
Kennell Prog Nucl Acid Res Mol Biol 11:259-301, 1971.*
Nathwani Amit C et al., "Self-complementary adeno-associated virus vectors containing a novel liver-specific human factor IX expression cassette enable highly efficient transduction of murine and nonhuman primate liver," Blood, Apr. 1, 2006, vol. 107, No. 7.
PCT International Search Report for International Application No. PCT/EP2009/054724, mailed Oct. 6, 2009.

* cited by examiner

*Primary Examiner* — Marcia S Noble
(74) *Attorney, Agent, or Firm* — TraskBritt P.C.

(57) ABSTRACT

The present invention relates to nucleic acid regulatory elements that are able to enhance liver-specific expression of genes, methods employing these regulatory elements and uses of these elements. Expression cassettes and vectors containing these nucleic acid regulatory elements are also disclosed. The present invention is particularly useful for applications using gene therapy.

18 Claims, 3 Drawing Sheets

LIVER-SPECIFIC NUCLEIC ACID REGULATORY ELEMENTS AND METHODS AND USE THEREOF

CROSS-REFERENCE TO RELATED APPLICATION(S)

This application is a national entry under 35 U.S.C. §317 of PCT International Application Number PCT/EP2009/054724 filed on Apr. 21, 2009, which published, in English, as International Publication Number WO 2009/130208 A1, and claims priority under Article 8 of the Patent Cooperation Treaty to U.S. Provisional Patent Application 61/125,181, filed on Apr. 22,2008.

FIELD OF THE INVENTION

The present invention relates to nucleic acid regulatory elements that are able to enhance liver-specific expression of genes, methods employing these regulatory elements and uses of these elements. Expression cassettes and vectors containing these nucleic acid regulatory elements are also disclosed. The present invention is particularly useful for applications using gene therapy.

BACKGROUND

The liver fulfils a great variety of essential functions in the body, including the synthesis of proteins involved in metabolism, hemostasis, and protection against infection. Many acquired, complex and genetic diseases (hepatic diseases sensu stricto as well as some hereditary disorders that do not directly lead to liver disease but manifest themselves primarily elsewhere in the body) are associated with altered gene expression in the liver. Some examples include hemophilia A or B, familial hypercholesterolemia, ornithine transcarbamylase deficiency, or α-antitrypsin deficiency. In addition, the liver often falls prey to infections with pathogens (such as hepatitis viruses). Finally, the liver can undergo malignant transformation and give rise to liver cancer (hepatocellular carcinoma) or functionally degenerate as a consequence of pharmaceutical treatments and chemotherapy, drug or alcohol abuse. Consequently, there has been substantial and increasing interest in the use of gene therapy to express a functional gene in the liver to replace a needed protein or to block the expression of an altered or undesired gene product, for instance by RNA interference or dominant-negative inhibitory proteins, or to restore hepatocyte function in a degenerating liver. Transduction of hepatic cells with appropriate genes, such as immunostimulatory cytokines, may also be useful to induce immune responses against e.g. viral hepatitis or liver neoplasms (Barajas et al., 2001; Villa et al., 2001).

One of the major challenges in liver gene therapy is the achievement of hepato-specific therapeutic gene expression (Xia et al., 2004; Prieto et al., 2003). In vivo targeting of mammalian hepatocytes has been done by injecting DNA or viral vectors into the liver parenchyma, hepatic artery, or portal vein. Adenoviral vectors, even when administered systemically, target mainly the liver in mice (Wood et al., 1999) but can also infect lung and skeletal muscle. Moreover, the liver specificity of adenovirus has not yet been demonstrated in humans. Other vectors, like adeno-associated viral vectors (AAV) or lentiviral vectors, can also transduce hepatocytes, but again transduction of non-hepatic cells can occur leading to off-target gene expression (VandenDriessche et al., 2002). Another method to localize gene expression is by transcriptional targeting. In general, transcriptional targeting is highly desirable for all in vivo gene therapy applications as it can prevent expression of the transgene in non-target cells, thus mimicking physiological regulation (Tenenbaum et al., 2003; Schagen et al., 2004). The use of proper liver-specific transcriptional elements should restrict the expression of a therapeutic gene to hepatocytes. For instance, some promoters that are active mainly in the liver have already been used for cell-specific gene delivery (Kuriyama et al., 1991; Kistner et al., 1996). However, functional tissue specificity has only rarely been demonstrated. Furthermore, major disadvantages for the use of liver-specific promoters in gene therapy are the large size, since many vectors have a restricted cloning space, and/or the low activity compared to strong (viral) promoters, such as cytomegalovirus (CMV) or long terminal repeat (LTR) promoter sequences, widely used in gene therapy protocols.

Increasing tissue-specific transgene expression is desirable as a way to decrease the amount of viral vector required to achieve a clinical effect. To increase both specificity and activity, the use of cis-acting regulatory elements has been proposed. Typically, this concerns enhancer sequences, i.e. nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter. For the liver, numerous approaches to incorporate such organ-specific regulatory sequences into retroviral, lentiviral, adenoviral and adeno-associated viral vectors or non-viral vectors (often in addition to housekeeping hepatocyte-specific cellular promoters) have been reported so far (Ferry et al., 1998; Ghosh et al., 2000; Miao et al., 2000; Follenzi et al., 2002). Advantages of restricting vector-mediated gene expression to hepatocytes by using liver-specific promoters and enhancers include e.g., reducing the probability of inducing an immune response to the protein encoded by the transgene (Pastore et al., 1999; Brown et al., 2006, 2007).

Several enhancer sequences for liver-specific genes have been documented. WO95/011308 describes a gene therapy vector comprising a hepatocyte-specific control region (HCR) enhancer linked to a promoter and a transgene. The human apolipoprotein E-Hepatocyte Control Region (ApoE-HCR) is a locus control region (LCR) for liver-specific expression of the apolipoprotein E (ApoE) gene. The ApoE-HCR is located in the ApoE/CI/CII locus, has a total length of 771 bp and is important in expression of the genes ApoE and ApoC-I in the liver (Simonet et al., 1993). In WO01/098482, the combination of this specific ApoE enhancer sequence or a truncated version thereof with hepatic promoters is suggested. It was shown that vector constructs combining the (non-truncated) ApoE-HCR enhancer with a human α-antitrypsin (AAT) promoter were able to produce the highest level of therapeutic protein in vivo (Miao et al., 2000) and may confer sustained expression when used in conjunction with a heterologous transgene (Miao et al., 2001). Of note, these authors not only demonstrate the importance of cis sequences for enhancing in vivo hepatic gene expression, but also reemphasize the lack of correlation of gene expression in tissue culture and in vivo studies.

This ApoE-HCR-AAT expression cassette as used e.g. in the pAAV-ApoHCR-AAT-FIXIA construct (VandenDriessche et al., 2007) is one of the most potent liver-specific FIX expression constructs known, and has been successfully applied in a phase ½ dose-escalation clinical study in humans with severe hemophilia B (Manno et al., 2006). The expression of this hFIX minigene is driven from an ApoE-HCR joined to the human AAT promoter. The 5'-flanking sequence of the human AAT gene contains multiple cis-regulatory elements, including a distal enhancer and proximal sequences, with a total length of around 1.2 kb. It was shown to be sufficient to confer tissue specificity in vivo by driving gene expression primarily in the liver and also, to a lesser extent, in other tissues known to express AAT (Shen et al., 1989). A 347 bp fragment of this 1.2 kb region in combination with the ApoE enhancer is capable of achieving long-term liver-specific gene expression in vivo (Le et al., 1997). Interestingly, this shorter promoter targets expression to the liver with a greater specificity than that reported for larger AAT promoter fragments (Yull et al., 1995).

Other chimeric liver-specific constructs have also been proposed in the literature, e.g. with the AAT promoter and the albumin or hepatitis B enhancers (Kramer et al., 2003), or the alcohol dehydrogenase 6 (ADH6) basal promoter linked to two tandem copies of the apolipoprotein E enhancer element (Gehrke et al., 2003). The authors of the latter publication stress the importance of the relatively small size (1068 bp) of this enhancer-promoter combination.

To be able to provide a therapeutic level of the transgene product for an extended time period, gene transfer vectors preferably allow specifically regulated, high expression, while at the same time retaining sufficient cloning space for the transgene to be inserted, i.e. the regulatory elements used to achieve the high and tissue-specific expression preferably are of only limited length. However, none of the gene therapy vectors disclosed thus far satisfies all these criteria. Instead, gene therapy vectors are not sufficiently robust in terms of either expression levels and/or specificity of expression in the desired target cells, particularly the hepatocyte. Decreasing the promoter/enhancer size often compromised the expression levels and/or expression specificity whereas the use of larger sequences often compromises the efficiency of gene delivery due to impaired vector function, packaging and/or transfection/transduction efficiency. Thus, there is a need in the art for vectors that achieve therapeutic levels of transgene expression in the liver for effective gene therapy.

SUMMARY OF THE INVENTION

It is an object of the present invention to increase efficiency of liver-specific expression of constructs used for gene therapy, particularly in vivo. At the same time, it is an object of the invention to achieve this using constructs with a high degree of structural compactness. The above objective is accomplished by providing specific regulatory elements that enhance promoter expression, while retaining tissue specificity (even when minimal promoters are used). Of particular importance is the small size of these regulatory elements, which makes it possible to accommodate this transcriptional control unit in any type of viral or non-viral vector, even in conjunction with large effector genes. Despite their limited length, the regulatory elements provided herein are able to enhance expression of a transgene to similar and typically even higher levels when compared to traditional, longer nucleic acid expression cassettes used in gene therapy.

Thus, according to a first aspect, nucleic acid regulatory elements of 600 nucleotides or less are provided for enhancing liver-specific gene expression, comprising a sequence selected from the group consisting of: SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof.

According to a further particular embodiment, the nucleic acid regulatory element comprises a sequence selected from the group consisting of: SEQ ID NO: 3, SEQ ID NO: 1, SEQ ID NO: 2, a sequence having 95% identity to any of these sequences, or a functional fragment thereof. According to yet a further particular embodiment, the nucleic acid regulatory element comprises SEQ ID NO: 3, a sequence having 95% identity to any of these sequences, or a functional fragment thereof.

According to an alternative embodiment, nucleic acid regulatory elements are provided of 600 nucleotides or less hybridizing under stringent conditions to the regulatory element comprising a sequence selected from the group consisting of: SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof.

According to a further alternative embodiment, nucleic acid regulatory elements of 600 nucleotides or less are provided, comprising at least two fragments of sequences selected from the group consisting of: SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and a sequence having 95% identity to any of these sequences. According to a further particular embodiment, at least two of these fragments are different from each other. According to yet a further particular embodiment, all fragments are different from each other. According to an alternative particular embodiment, at least two fragments are identical. According to another specific embodiment, at least one of the at least two fragments is a functional fragment. According to a further specific embodiment, all fragments are functional fragments of the listed sequences.

In a further aspect, the regulatory elements are used to express genes or transgenes. Accordingly, nucleic acid expression cassettes are provided comprising a nucleic acid regulatory element as described herein, operably linked to a promoter. According to a further embodiment of this aspect, the nucleic acid regulatory element in the nucleic acid expression cassettes is operably linked to a promoter and a transgene.

According to a specific embodiment, the nucleic acid expression cassettes are provided with two or more nucleic acid regulatory elements. These two or more nucleic acid regulatory elements are then operably linked to the promoter, and optionally the transgene. According to a further specific embodiment, at least two of the two or more regulatory elements are identical or substantially identical (e.g. 90% or 95% identical). According to yet a further specific embodiment, all of the two or more regulatory elements are identical or substantially identical. According to an alternative specific embodiment, at least two of the two or more regulatory elements are not identical to each other.

According to a particular embodiment, the promoter contained in the nucleic acid expression cassettes provided is a liver-specific promoter. According to a further particular embodiment, the liver-specific promoter is from the transthyretin (TTR) gene. According to yet a further particular embodiment, the TTR promoter is a minimal promoter, most particularly a minimal promoter as defined in SEQ ID NO: 17.

According to another particular embodiment, the promoter contained in the nucleic acid expression cassettes provided is a minimal promoter.

The transgene that may be contained in the nucleic acid expression cassette typically encodes a gene product such as RNA or a polypeptide (protein). According to a specific embodiment, the transgene encodes a therapeutic protein. According to a further specific embodiment, the therapeutic protein is a clotting factor. According to still a further specific embodiment, the therapeutic protein (or clotting factor) is factor IX.

The nucleic acid expression cassette, and even the regulatory element, as described herein may be used as such. However, in typical embodiments, the expression cassette will be part of a nucleic acid vector. Accordingly, in a further aspect vectors are provided comprising the regulatory element as described herein. According to a particular embodiment, the vectors comprise the nucleic acid expression cassette as disclosed in the application.

According to a specific embodiment, the vectors provided are viral vectors, in particular retroviral, lentiviral, adenoviral or AAV vectors, more in particular lentiviral or AAV vectors. According to an alternative embodiment, the vectors are non-viral vectors. According to yet another alternative embodiment, the vectors contain both viral and non-viral elements.

It is evident to the skilled person that the liver-specific regulatory elements, the nucleic acid expression cassettes and the vectors containing either may be used for gene therapy purposes. Accordingly, the use of the nucleic acid regulatory element as described herein in gene therapy is envisaged. According to another particular embodiment, use of the nucleic acid expression cassettes as disclosed herein in gene therapy is disclosed. According to yet a further particular embodiment, the application envisages the use of vectors as described herein for gene therapy. According to a particular embodiment, the gene therapy envisaged is liver-specific gene therapy. According to another particular embodiment, the gene therapy is gene therapy for a disease originating in the liver.

According to a further aspect of the invention, methods for expressing a transgene product in liver cells are provided, comprising the steps of:
introducing in liver cells the nucleic acid expression cassette wherein a nucleic acid regulatory element as described herein is operably linked to a promoter and a transgene;
expressing the transgene product in the liver cells.

According to a further particular embodiment, the transgene product is a protein. According to yet a further particular embodiment, the protein is a therapeutic protein. According to an alternative embodiment, the transgene product is RNA. According to another particular embodiment, the methods are performed in vitro. According to an alternative particular embodiment, the methods are performed ex vivo. According to an alternative particular embodiment, the methods are performed in vivo.

Methods of gene therapy for a subject in need thereof are also provided herein. These methods typically comprise the steps of:
introducing in the liver of the subject a nucleic acid expression cassette wherein a nucleic acid regulatory element as described herein is operably linked to a promoter and a transgene encoding a therapeutic protein;
expressing a therapeutic amount of the (therapeutic) protein in the liver.

Instead of introducing the nucleic acid expression cassette as such, the methods may also introduce in the liver of the subject a vector containing a nucleic acid expression cassette wherein a nucleic acid regulatory element as described herein is operably linked to a promoter and a transgene encoding a therapeutic protein.

In general, the subject in need thereof will be a mammal, most particularly a human. Typically, the subject in need thereof will have certain symptoms, most particularly symptoms characteristic of a disease. According to a further particular embodiment, the methods additionally comprise the step of ameliorating the symptoms of the subject in need thereof, by expressing the therapeutic amount of the therapeutic protein.

According to a particular embodiment, the methods may be used for the treatment of a subject with hemophilia B. According to this embodiment, the methods comprise the steps of:
introducing in the liver of the subject a nucleic acid expression cassette wherein a nucleic acid regulatory element as described herein is operably linked to a promoter and a transgene encoding a clotting factor, in particular factor IX, or a vector comprising such nucleic acid expression cassette;
expressing a therapeutic amount of the clotting factor (in particular factor IX) in the liver.

These methods may further comprise the step of ameliorating the symptoms of hemophilia B by expressing the therapeutic amount of the clotting factor (in particular factor IX) in the liver.

DETAILED DESCRIPTION

Definitions

Figure 1:
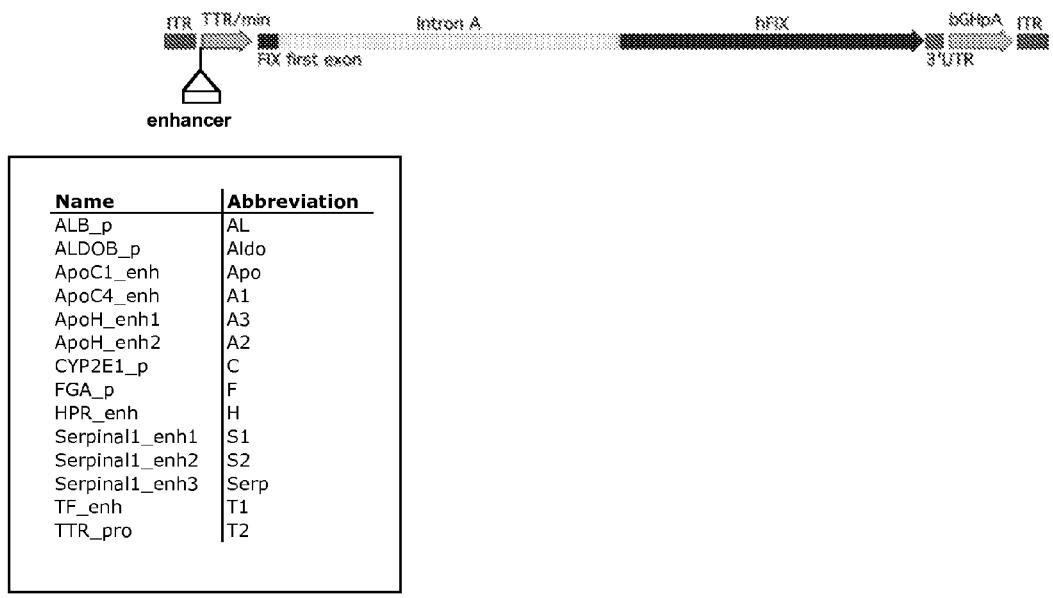
FIG. 1 shows a schematic diagram of the pAAV-TTRmin (E)-FIXIA construct with indication where the different liver-specific enhancers are inserted upstream of the transthyretin minimal promoter. The names and abbreviations of the enhancers are listed in the table below the construct. Abbreviations used are: ITR: viral inverted terminal repeat; TTRmin: transthyretin minimal promoter; FIX first exon: first exon of the human factor IX gene; Intron A: 1.4 kb fragment of the first intron of the human factor IX gene; hFIX: exons 2 to 8 of the human factor IX gene; 3'UTR: 3' untranslated region of the human factor IX gene, truncated at 70 bp; bGHpA: polyadenylation signal of bovine growth hormone.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

A 'regulatory element' as used herein refers to transcriptional control elements, in particular non-coding cis-acting transcriptional control elements, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a liver-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically are naturally occurring sequences, combinations of (parts of) such regulatory elements or several copies of a regulatory element, i.e. non-naturally occurring sequences, are themselves also envisaged as regulatory element. Regulatory elements as used herein may be part of a larger sequence involved in transcriptional control, e.g. part of a promoter sequence. However, regulatory elements alone are typically not sufficient to initiate transcription, but require a promoter to this end.

'Liver-specific expression', as used in the application, refers to the preferential or predominant expression of a (trans)gene (as RNA and/or polypeptide) in the liver as compared to other tissues. According to particular embodiments, at least 50% of the (trans)gene expression occurs within the liver. According to more particular embodiments, at least 60%, at least 70%, at least 75%, at least 80%, at least 85%, at least 90%, at least 95%, at least 97%, at least 99% or 100% of the (trans)gene expression occurs within the liver. According to a particular embodiment, liver-specific expression entails that there is no 'leakage' of expressed gene product to other organs, such as spleen, muscle, heart and/or lung. The same applies mutatis mutandis for hepatocyte-specific expression, which may be considered as a particular form of liver-specific expression. Throughout the application, where liver-specific is mentioned in the context of expression, hepatocyte-specific expression is also explicitly envisaged. Similarly, where tissue-specific expression is used in the application, cell-type specific expression of the cell type(s) predominantly making up the tissue is also envisaged.

The term 'functional fragment' as used in the application refers to fragments of the sequences disclosed herein that retain the capability of regulating liver-specific expression, i.e. they still confer tissue specificity and they are capable of regulating expression of a (trans)gene in the same way (although possibly not to the same extent) as the sequence from which they are derived. Fragments comprise at least 10 contiguous nucleotides from the sequence from which they are derived. In further particular embodiments, fragments comprise at least 15, at least 20, at least 25, at least 30, at least 35 or at least 40 contiguous nucleotides from the sequence from which they are derived.

The term 'hybridize under stringent conditions', and grammatical equivalents thereof, refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature ($T_m$) of the native duplex. Methods of calculating $T_m$ are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours. (See generally, Sambrook et al. Molecular Cloning: A Laboratory Manual, 2nded., Cold Spring Harbor Press, 1987; Ausubel et al., Current Protocols in Molecular Biology, Greene Publishing, 1987).

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid sequence is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers). In the context of the present application, a promoter is typically operably linked to regulatory elements to regulate transcription of a transgene. When a regulatory element as described herein is operably linked to both a promoter and a transgene, the regulatory element can (1) confer a significant degree of liver specific expression in vivo (and/or in hepatocytes/hepatic cell lines in vitro) of the transgene, and/or (2) can increase the level of expression of the transgene in the liver (and/or in hepatocytes/hepatocyte cell lines in vitro). A 'minimal promoter' as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Minimal promoters have been extensively documented in the art, a non-limiting list of minimal promoters is provided in the specification.

The term 'transgene' as used herein refers to particular nucleic acid sequences encoding a polypeptide or a portion of a polypeptide to be expressed in a cell into which the nucleic acid sequence is inserted. However, it is also possible that transgenes are expressed as RNA, typically to lower the amount of a particular polypeptide in a cell into which the nucleic acid sequence is inserted. These RNA molecules include but are not limited to molecules that exert their function through RNA interference (shRNA, RNAi), micro-RNA regulation (miR), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is inserted. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. In some cases, the transgene may also include a sequence encoding a leader peptide or signal sequence such that the transgene product will be secreted from the cell.

The term 'vector' as used in the application refers to nucleic acid molecules, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, etc. Viral vectors are derived from viruses and include but are not limited to retroviral, lentiviral, adeno-associated viral, adenoviral, herpesviral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis.

According to a first aspect of the invention, nucleic acid regulatory elements for enhancing liver-specific gene expression are provided of 600 nucleotides or less, comprising a sequence selected from the group consisting of: SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14. According to a specific embodiment, the nucleic acid regulatory elements comprise a sequence having 80% sequence identity, more in particular 85% sequence identity, even more in particular 90% sequence identity, yet even more in particular 95%, 98% or 99% sequence identity to any of these sequences. According to another specific embodiment, the nucleic acid regulatory elements comprise a functional fragment of these sequences (or of the sequences sharing high percentage sequence identity with these sequences). How the sequences involved in liver-specific gene expression were identified is outlined in the examples section.

It is a considerable benefit that the regulatory elements as described herein are fully functional while being only of limited length. This allows their use in vectors or nucleic acid expression cassettes without unduly restricting their payload capacity. Accordingly, the nucleic acid regulatory elements are 600 nucleotides or less in length, 550 nucleotides or less, 500 nucleotides or less, 450 nucleotides or less, 400 nucleotides or less, 350 nucleotides or less, more in particular 300 nucleotides or less, 250 nucleotides or less, 200 nucleotides or less, 175 nucleotides or less, even more in particular 150 nucleotides or less, 125 nucleotides or less, 110 nucleotides or less, yet even more in particular 100 nucleotides or less, 90 nucleotides or less, 80 nucleotides or less, 75 nucleotides or less, 70 nucleotides or less, 65 nucleotides or less, 60 nucleotides or less, 55 nucleotides or less, 50 nucleotides or less. However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides or 50 nucleotides.

Furthermore, according to particular embodiments, the nucleic acid regulatory elements of 600 nucleotides or less for enhancing liver-specific gene expression consist essentially of SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof. That is to say, the regulatory element may for instance additionally comprise sequences used for cloning purposes (see for an arbitrary example the sequences provided as SEQ IDs 18-31), but the aforementioned sequences make up the essential part of the regulatory element, e.g. they do not form part of a larger regulatory region such as a promoter. According to a further particular embodiment, the nucleic acid regulatory elements of 600 nucleotides or less for enhancing liver-specific gene expression consist of SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof.

The nucleic acid sequences may be provided as DNA or RNA, as double stranded or single stranded molecule. In case the sequences are provided as single stranded nucleic acids, the complement strand is considered equivalent to the disclosed SEQ IDs, and is also envisaged for use in the nucleic acid constructs and methods and uses thereof described herein. Thus, according to a specific embodiment, the nucleic acid regulatory elements comprise the complement strand of SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or of a functional fragment thereof. According to a further specific embodiment, the regulatory elements consist essentially of the complement strand of the aforementioned sequences. According to yet a further specific embodiment, the regulatory elements consist of the complement strand of the listed sequences.

Furthermore, it is envisaged that sequences hybridizing to the sequences listed herein, in particular hybridizing to the complement of the sequences disclosed herein, can also be used as nucleic acid regulatory elements. With hybridizing is typically meant 'hybridizing under stringent conditions'. Sequences hybridizing to the listed sequences do not need to be of equal length as the sequence they hybridize to. However, it is to be noted that these hybridizing sequences, to be used as nucleic acid regulatory elements, particularly do not exceed the size limit for the regulatory elements as described herein. Moreover, according to a specific embodiment, the size of the nucleic acid hybridizing to SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof, does not differ more than 25% in length, in particular 20% in length, more in particular 15% in length, most in particular not more than 10% in length from the sequence it hybridizes to.

Several of the sequences disclosed herein are very limited in length; some are also considerably shorter than others. Thus, particularly for the shorter sequences, it is possible to make a regulatory element that comprises two or more copies of the same sequence, or even two different sequences of the listed sequences. Although modularly combining sequences (or copies of the same sequence) is of course possible for all sequences, it is particularly envisaged for those combinations of sequences that do not exceed the size of the regulatory element as defined herein, i.e. do not exceed 600 nucleotides (or more in particular do not exceed 400 nucleotides or even more in particular do not exceed 300 or 250 nucleotides). According to a very specific embodiment, nucleic acid regulatory elements disclosed herein comprise at least two functional fragments of the listed sequences, combined to make a new (artificial) regulatory sequence. According to a further specific embodiment, these at least two functional fragments are non-identical fragments. According to an alternative embodiment, at least two of the at least two functional fragments are identical to each other. According to another very specific embodiment, two fragments of the listed sequences, at least one of which is not functional as such, are combined to make a new (artificial) regulatory sequence.

Sequences disclosed herein are regulatory sequences controlling transcription of liver-specific genes in vivo, in particular controlling the following genes: serpin peptidase inhibitor, clade A member 1, also known as α-antitrypsin (SERPINA1; GeneID 5265), apolipoprotein C-I (APOC1; GeneID 341), apolipoprotein C-IV (APOC4; GeneID 346), apolipoprotein H (APOH; GeneID 350); transthyretin (TTR; GeneID 7276), albumin (ALB; GeneID 213), aldolase B (ALDOB; GeneID 229), cytochrome P450, family 2, subfamily E, polypeptide 1 (CYP2E1; GeneID 1571), fibrinogen alpha chain (FGA; GeneID 2243), transferrin (TF; GeneID 7018), haptoglobin related protein (HPR; GeneID 3250). According to a specific embodiment, the regulatory elements comprise SERPINA1 regulatory elements, i.e. regulatory elements that control expression of the SERPINA1 gene in vivo. According to a further specific embodiment, the regulatory elements comprise SERPINA1 regulatory sequences selected from SEQ ID NO: 3, SEQ ID NO: 1, SEQ ID NO: 2. According to yet a further specific embodiment, the regulatory element comprises SEQ ID NO: 3.

The nucleic acid regulatory elements disclosed herein can be used in a nucleic acid expression cassette. Thus, according to one aspect of the invention, nucleic acid expression cassettes are provided wherein a regulatory element as described herein is operably linked to a promoter. According to a further embodiment, the regulatory element is operably linked to a promoter and a transgene.

As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Thus, according to a specific embodiment, the regulatory or enhancing effect of the regulatory sequences is position-independent. Moreover, the regulatory sequences are able to exert their effect on expression independent of particular promoter or gene sequences.

Thus, they can be used in nucleic acid expression cassettes in conjunction with their natural promoter, as well as with another promoter. In particular, the regulatory elements are able to direct tissue-specific expression even from a promoter that itself is not liver-specific (or lacks elements which contribute to making it liver-specific, in the case of minimal promoters). However, liver-specific promoters may of course also be used, to increase liver-specificity and/or avoid leakage of expression in other tissues. The liver-specific promoter may or may not be a hepatocyte-specific promoter. The promoter does not need to be the promoter of the transgene in the nucleic acid expression cassette, although it is possible that the transgene is transcribed from its own promoter. According to a particular embodiment, the nucleic acid expression cassette is used for gene therapy. According to this embodiment, the promoter may be homologous (i.e. from the same species as the animal (in particular mammal) to be transfected with the nucleic acid expression cassette) or heterologous (i.e. from a source other than the species of the mammal to be transfected with the expression cassette). As such, the source of the promoter may be any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. According to a specific embodiment, the promoter is a mammalian promoter, in particular a murine or human promoter. According to a further specific embodiment, the promoter is a mammalian liver-specific promoter. According to yet a further specific embodiment, the promoter is a human liver-specific promoter. According to an alternative embodiment, the promoter is a viral promoter. According to a further embodiment, the viral promoter is a liver-specific viral promoter. The promoter may be an inducible or constitutive promoter.

To minimize the length of the nucleic acid expression cassette, it is particularly envisaged that the regulatory elements are linked to minimal promoters. According to a particular embodiment, the promoter used is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less. Examples of promoters that may be used include, but are not limited to, the ApoA-I promoter, the ApoA-II promoter, the ApoA-IV promoter, the ApoB promoter, the ApoC-I promoter, the ApoC-II promoter, the ApoC-III promoter, the ApoE promoter, the albumin promoter, the α-fetoprotein promoter, the phosphoenolpyruvate carboxykinase 1 (PCK1) promoter, the phosphoenolpyruvate carboxykinase 2 (PCK2) promoter, the transthyretin (TTR) promoter, the α-antitrypsin (AAT or SERPINA1) promoter, the TK (thymidine kinase) promoter, the hemopexin promoter, the alcohol dehydrogenase 6 promoter, the cholesterol 7alpha-hydroxylase promoter, the factor IX promoter, the α-microglobulin promoter, the SV40 promoter, the CMV promoter, the Rous Sarcoma Virus-LTR promoter and the HBV promoter. Any of these promoters may also be used as a minimal promoter, which have been well documented in the art (see e.g. Gehrke et al., 2003; Vandendriessche et al., 2007; WO01/098482). A particularly envisaged minimal promoter is the TTR minimal promoter, more particularly as defined in SEQ ID NO: 17. Sometimes minimal promoters are referred to as basal or core promoters. Although these may differ somewhat with regard to which sequences are lacking in the promoter, all such promoters lacking (part of) their regulatory sequences are envisaged within the definition of minimal promoters.

The regulatory sequences as disclosed herein may be used in the nucleic acid expression cassettes. According to a particular embodiment, only one regulatory element is included in the expression cassette. According to an alternative particular embodiment, more than one regulatory element is included in the nucleic acid expression cassette, i.e. they are combined modularly to enhance their regulatory (and/or enhancing) effect. According to a further particular embodiment, two or more copies of the same regulatory element are used in the nucleic acid expression cassette. For instance, 2, 3, 4, 5, 6, 7, 8, 9, 10 copies of a regulatory element may be provided as tandem repeats. According to another further particular embodiment, the more than one regulatory element included in the nucleic acid expression cassette comprises at least two different regulatory elements. Both embodiments are not mutually exclusive, it is possible to combine both identical and non-identical regulatory elements with each other in the nucleic acid expression cassettes described herein. Since the combination of regulatory elements will function as one regulatory element in the nucleic acid expression cassette, this embodiment is largely equivalent to the combinations of sequences in one regulatory element. However, as each of the sequences functions as regulatory element as such, it is preferred to refer to them as a combination of regulatory sequences, and to nucleic acid expression cassettes containing more than one regulatory sequence. Although in theory, there is no upper limit to the number of regulatory elements that can be included in the expression cassette (other than the feasibility of cloning), it is according to one embodiment particularly envisaged that the length of the total regulatory element(s) in the nucleic acid expression cassette does not exceed 1000 nucleotides. According to further particular embodiments, the total length of the regulatory elements does not exceed 900 nucleotides, 800 nucleotides, 750 nucleotides, 700 nucleotides, 600 nucleotides, 550 nucleotides, 500 nucleotides, 450 nucleotides, 400 nucleotides, 350 nucleotides, 300 nucleotides, 250 nucleotides, 200 nucleotides, 175 nucleotides, 150 nucleotides, 125 nucleotides, 110 nucleotides, 100 nucleotides, 90 nucleotides, 80 nucleotides, 75 nucleotides, 70 nucleotides, 65 nucleotides, 60 nucleotides, 55 nucleotides or 50 nucleotides. However, the minimal length defined for the regulatory elements also applies to regulatory elements or combinations thereof used in nucleic acid expression cassettes.

As the payload of the nucleic acid expression cassette is influenced both by promoter and regulatory element(s), it is envisaged that according to a particular embodiment, the total length of the promoter and regulatory elements in the nucleic acid expression cassette is 1000 nucleotides or less, 900 nucleotides or less, 800 nucleotides or less, 750 nucleotides or less, 700 nucleotides or less, 600 nucleotides or less, 550 nucleotides or less, 500 nucleotides or less, 450 nucleotides or less, 400 nucleotides or less, 350 nucleotides or less, 300 nucleotides or less, or even 250 nucleotides or less.

According to a very specific embodiment, the nucleic acid regulatory elements are the only regulatory (and/or enhancing) elements in the nucleic acid expression cassette, there are e.g. no regulatory elements present any more in the promoter, or no additional enhancers in the construct. According to a further specific embodiment, the sequences selected from the group of SEQ ID NO: 3, SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, a sequence having 95% identity to any of these sequences, or a functional fragment thereof are the sole regulatory (and/or enhancing) sequences present in either the regulatory element or the nucleic acid expression cassette, i.e. the regulatory element does not contain other regulatory or enhancing sequences.

As already indicated, the regulatory sequences are able to exert their effect on expression independent of particular promoter or (trans)gene sequences. The nature of the (trans) gene accordingly is not vital to the invention, as long as the operably linked promoter and regulatory element are successful in transcribing the sequence. According to particular embodiments, the nucleic acid expression cassettes will be used in gene therapy, and the transgene will be primarily expressed in the liver. In some cases, the gene product may also be secreted into the bloodstream after synthesis. Thus, included within the scope of this application is any transgene encoding a nucleic acid (e.g. RNA) and/or a polypeptide to be circulated in the blood.

Typically, the transgene will be a nucleic acid molecule encoding a polypeptide involved in the immune response, hematopoiesis, inflammation, cell growth and proliferation, cell lineage differentiation, and/or the stress response.

The transgene may be homologous or heterologous to the promoter (and/or to the animal, in particular mammal, in which it is introduced, in cases where the nucleic acid expression cassette is used for gene therapy). In addition, the transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. The transgene may also optionally be a mutant of one or more naturally occurring cDNA and/or genomic sequences.

The transgene may be isolated and obtained in suitable quantity using one or more methods that are well known in the art. These methods and others useful for isolating a transgene are set forth, for example, in Sambrook et al. (supra) and in Berger and Kimmel (Methods in Enzymology: Guide to Molecular Cloning Techniques, vol. 152, Academic Press, Inc., San Diego, Calif. (1987)).

The use of transgene mutant sequences is also contemplated in the application. A mutant transgene is a transgene containing one or more nucleotide substitutions, deletions, and/or insertions as compared to the wild type sequence. The nucleotide substitution, deletion, and/or insertion can give rise to a gene product (i.e. e., protein or RNA) that is different in its amino acid/nucleic acid sequence from the wild type amino acid/nucleic acid sequence. Preparation of such mutants is well known in the art.

According to a particular embodiment, the product encoded by the transgene is a protein. According to a further particular embodiment, the product is a therapeutic protein.

A non-exhaustive and non-limiting list of transgenes (and therapeutic proteins) envisaged in the application includes factor VIII, factor IX, factor VII, factor X, von Willebrand factor, erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), afamin (AFM), α1-antitrypsin, α-galactosidase A, α-L-iduronidase, ATP7b, ornithine transcarbamoylase, phenylalanine hydroxylase, lipoprotein lipase, apoliproteins, low-density lipoprotein receptor (LDL-R), albumin, glucose-6-phosphatase, transgenes encoding antibodies, nanobodies, anti-viral dominant-negative proteins, and fragments, subunits or mutants thereof.

According to a very specific embodiment, the nucleic acid expression cassette does not contain a transgene, but the regulatory element(s) operably linked to the promoter are used to drive expression of an endogenous gene (that thus is equivalent to the transgene in terms of enhanced and/or tissue-specific expression). The nucleic acid expression cassette may be integrated in the genome of the cell or stay episomal.

Other sequences may be incorporated in the nucleic acid expression cassette as well, typically to further increase or stabilize the expression of the transgene product (e.g. introns and/or polyadenylation sequences). Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal.

Any polyadenylation signal that directs the synthesis of a poly A tail is useful in the expression cassettes described herein, examples of those are well known to one of skill in the art (e.g. the bovine growth hormone polyadenylation signal).

The expression cassettes described in the application can be used, for example, to express proteins that are normally expressed and utilized in the liver, or to express proteins that are expressed in the liver and are then exported to the blood stream for transport to other portions of the body (such as Factor IX protein). Thus, according to some particular embodiments, the expression cassettes of the invention can be used to express a therapeutic amount of a polypeptide (or other gene product, such as RNA) to ameliorate the symptoms of a disease. Typically, the gene product is encoded by the coding sequence within the expression cassette (i.e. the transgene), although in principle it is also possible to increase expression of an endogenous gene. A 'therapeutic amount' as used herein is an amount that ameliorates the symptoms of a disease. Such amount will typically depend on the gene product and the severity of the disease, but can be decided by the skilled person, possibly through routine experimentation. In the Examples section it is described how therapeutic amounts of factor IX expression are achieved.

According to a particular embodiment, the expression cassettes described in this application direct the expression of a therapeutic amount of the gene product encoded by the coding sequence for an extended period. Indeed, as long as therapeutic levels are achieved, no new treatment is necessary. Typically, therapeutic expression is envisaged to last at least 20 days, at least 50 days, at least 100 days, at least 200 days, and in some instances 300 days or more. Expression of the gene product (e.g. polypeptide) encoded by the coding sequence can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

In a further aspect, the present application provides vectors that include a regulatory element as described herein. According to a further particular embodiment, the vectors contain an expression cassette as described herein. The vectors can be episomal vectors (i.e., that do not integrate into the genome of a host cell), or can be vectors that integrate into the host cell genome. Examples of episomal vectors include (extrachromosomal) plasmids and so-called mini-circles, which are composed of the expression cassette only and are devoid of bacterial sequences, and examples of vectors that integrate into the host cell genome including viral vectors.

Representative plasmid vectors include pUC vectors, bluescript vectors (pBS) and pBR322 or derivatives thereof that are devoid of bacterial sequences (minicircles). Some of the plasmid vectors can be adapted to incorporate elements that enhance episomal plasmid persistence in the transfected cells. Such sequences include S/MARs that correspond to scaffold/matrix attached region modules linked to a transcription unit (Jenke et al., 2004; Manzini et al., 2006).

Representative viral vectors include vectors derived from adeno-associated virus, adenovirus, retroviruses and lentiviruses. Alternatively, gene delivery systems can be used to combine viral and non-viral components, such as nanoparticles or virosomes (Yamada et al., 2003).

Retroviruses and lentiviruses are RNA viruses that have the ability to insert their genes into host cell chromosomes after infection. Retroviral and lentiviral vectors have been developed that lack the genes encoding viral proteins, but retain the ability to infect cells and insert their genes into chromosomes of the target cell (Miller, 1990; Naldini et al., 1996). The difference between a lentiviral and a classical Moloney-murine leukemia-virus (MLV) based retroviral vector is that lentiviral vectors can transduce both dividing and non-dividing cells whereas MLV-based retroviral vectors can only transduce dividing cells.

Adenoviral vectors are designed to be administered directly to a living subject. Unlike retroviral vectors, most of the adenoviral vector genomes do not integrate into the chromosome of the host cell. Instead, genes introduced into cells using adenoviral vectors are maintained in the nucleus as an extrachromosomal element (episome) that persists for an extended period of time. Adenoviral vectors will transduce dividing and nondividing cells in many different tissues in vivo including airway epithelial cells, endothelial cells, hepatocytes and various tumors (Trapnell, 1993).

Adeno-associated virus (AAV) is a small ssDNA virus which infects humans and some other primate species, not known to cause disease and consequently causing only a very mild immune response. AAV can infect both dividing and non-dividing cells and may incorporate its genome into that of the host cell. These features make AAV a very attractive candidate for creating viral vectors for gene therapy, although the cloning capacity of the vector is relatively limited.

Another viral vector is derived from the herpes simplex virus, a large, double-stranded DNA virus. Recombinant forms of the vaccinia virus, another dsDNA virus, can accommodate large inserts and are generated by homologous recombination.

According to a particular embodiment, the vector is a viral vector. According to further particular embodiments, the vector is an AAV vector. According to alternative embodiments, the vector is a lentiviral vector.

In a further particular aspect, the nucleic acid regulatory elements, the nucleic acid expression cassettes and the vectors described herein can be used in gene therapy. Gene therapy protocols, intended to achieve therapeutic gene product expression in target cells, in vitro, but also particularly in vivo, have been extensively described in the art. These include, but are not limited to, intramuscular injection of plasmid DNA (naked or in liposomes), interstitial injection, instillation in airways, application to endothelium, intra-hepatic parenchyme, and intravenous or intra-arterial administration (e.g. intra-hepatic artery, intra-hepatic vein). Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver viral vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993).

According to a particular embodiment, the use of the nucleic acid regulatory elements, nucleic acid expression cassettes or vectors as described herein is envisaged for gene therapy of liver cells. According to a further particular embodiment, the use of the regulatory elements, expression cassettes or vectors is for gene therapy in vivo. According to yet a further particular embodiment, the use is for a method of gene therapy to treat hemophilia, in particular to treat hemophilia B.

Gene transfer into mammalian hepatocytes has been performed using both ex vivo and in vivo procedures. The ex vivo approach requires harvesting of the liver cells, in vitro transduction with long-term expression vectors, and reintroduction of the transduced hepatocytes into the portal circulation (Kay et al., 1992; Chowdhury et al., 1991). In vivo targeting has been done by injecting DNA or viral vectors into the liver parenchyma, hepatic artery, or portal vein, as well as via transcriptional targeting (Kuriyama et al., 1991; Kistner et al., 1996). Recent methods also include intraportal delivery of naked DNA (Budker et al., 1996) and hydrodynamic tail vein transfection (Liu et al., 1999; Zhang et al., 1999).

According to a further aspect, methods for expressing a protein in liver cells are provided, comprising the steps of introducing in liver cells a nucleic acid expression cassette (or a vector) as described herein and expressing the transgene protein product in the liver cells. These methods may be performed both in vitro and in vivo.

Methods of gene therapy for a subject in need thereof are also provided, comprising the steps of introducing in the liver of the subject a nucleic acid expression cassette containing a transgene encoding a therapeutic protein, and expressing a therapeutic amount of the therapeutic protein in the liver.

According to a further embodiment, the method comprise the steps of introducing in the liver of the subject a vector comprising the nucleic acid expression cassette containing a transgene encoding a therapeutic protein, and expressing a therapeutic amount of the therapeutic protein in the liver.

According to a very specific embodiment, the therapeutic protein encoded by the transgene in the nucleic acid expression cassette is factor IX, and the method is a method for treating hemophilia B. By expressing factor IX in the liver via gene therapy, hemophilia B can be treated (Snyder et al., 1999).

According to another aspect, a pharmaceutical composition is provided comprising a nucleic acid expression cassette containing a transgene encoding a therapeutic protein, and a pharmaceutically acceptable carrier. According to another embodiment, the pharmaceutical composition comprises a vector containing the nucleic acid expression cassette containing a transgene encoding a therapeutic protein, and a pharmaceutically acceptable carrier. According to further particular embodiments, the transgene encodes factor IX and the pharmaceutical composition is for treating hemophilia B.

The use of regulatory elements as disclosed herein for the manufacture of these pharmaceutical compositions is also envisaged.

It is to be understood that although particular embodiments, specific constructions and configurations, as well as materials, have been discussed herein for devices according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

Identification of Liver-Specific Regulatory Sequences

Introduction

A computational approach to discover and characterize tissue-specific enhancer/regulatory modules was used. No prior knowledge of the motifs they contain is needed. The approach consists essentially of the following steps:

(1) identification of tissue-specific genes that are highly expressed based on statistical analysis of microarray expression data of normal tissues;

(2) extraction of the corresponding promoter sequences from publicly available genomic databases;

(3) identification of the regulatory modules and the motifs they contain, using a novel distance difference matrix (DDM) approach (De Bleser et al., 2007). With the DDM approach regulatory elements, both enhancers and silencers, were detected. These elements were then modeled as sets of the motifs they contain.

(4) Next, the genomic context of the highly expressing tissue-specific genes was searched for clusters of motifs that are part of these sets. If these clusters coincide with regions that are highly conserved within several species, these regions were considered as putative enhancer modules. Note that the same can be done for lowly expressing tissue-specific genes and putative silencer modules.

Validation of the candidate enhancer modules was done by testing whether inclusion in a minimal construct increases expression of a reporter gene (see Examples 2 and 3).

Distance Difference Matrix (DDM) Approach

As input for the DDM method a set of sequences upstream of the transcription start sites of 59 highly (over)expressed liver-specific genes and a set of equal size of sequences upstream of the transcription start sites of 59 under-expressed liver-specific genes were used. A list of the liver-specific genes is included in Table I, indicated by their Reference Sequence IDs (RefSeq release 28, March 2008, for sequence revision, see http://www.ncbi.nlm.nih.gov/entrez/sutils/girevhist.cgi). The aim of the DDM method was to identify the transcription factor binding sites that are strongly associated with either over- or under-expression.

TABLE I

Reference Sequence IDs of over- and under-expressed liver-specific genes the regulatory sequences of which were selected as input for the DDM method.

RefSeq IDs of liver-specific genes

| Over-expressed | | | Under-expressed | | |
|---|---|---|---|---|---|
| NM_000483 | NM_181755 | NM_004032 | NM_001679 | NM_006449 | NM_000112 |
| NM_000669 | NM_005525 | NM_022437 | NM_006636 | NM_001748 | NM_014629 |
| NM_000667 | NM_000045 | NM_001133 | NM_001673 | NM_001006613 | NM_018639 |
| NM_000668 | NM_194431 | NM_012205 | NM_006347 | NM_172056 | NM_004460 |
| NM_000773 | NM_194430 | NM_000463 | NM_001444 | NM_178234 | NM_032970 |
| NM_001443 | NM_000029 | NM_000767 | NM_001628 | NM_032926 | NM_018433 |
| NM_001063 | NM_000762 | NM_001014975 | NM_139207 | NM_003902 | NM_014313 |
| NM_000670 | NM_206933 | NM_031371 | NM_016156 | NM_017412 | NM_006803 |
| NM_145727 | NM_033294 | NM_000672 | NM_002086 | NM_052905 | NM_014782 |
| NM_000384 | NM_033304 | NM_000163 | NM_001527 | NM_015678 | NM_013262 |
| NM_000506 | NM_000680 | NM_022436 | NM_002475 | NM_014746 | NM_015484 |
| NM_000042 | NM_032958 | NM_004490 | NM_003161 | NM_005779 | NM_004227 |
| NM_080914 | NM_000063 | NM_005886 | NM_133640 | NM_004349 | NM_015087 |
| NM_001181 | NM_001995 | NM_005410 | NM_020117 | NM_001164 | NM_018444 |
| NM_003057 | NM_032951 | NM_004139 | NM_138962 | NM_000415 | NM_002718 |
| NM_000185 | NM_000583 | NM_000896 | NM_007085 | NM_003601 | NM_004426 |
| NM_003725 | NM_000508 | NM_000784 | NM_002902 | NM_198902 | NM_002210 |
| NM_000715 | NM_020980 | NM_001701 | NM_000933 | NM_152422 | NM_052822 |
| NM_001710 | NM_001461 | NM_014012 | NM_001483 | NM_033198 | NM_001448 |
| NM_000429 | NM_007220 | | NM_006353 | NM_181777 | |

The distance difference matrix approach has been described in detail elsewhere (De Bleser et al., 2007). In short, it can be expected that the responsiveness of the two sets of promoters of differentially regulated liver-specific genes to a given stimulus can be explained by transcription factor binding sites (TFBSs) shared by both sets of promoters, though this may not explain the direction of the response. Next to this common set of TFBSs, every set of promoters might bear one or more TFBSs that are more characteristic of the promoters of the up-regulated or of the down-regulated group of genes, and might explain, at least partially, the observed differential behavior. These 'differential' TFBSs can be found using the following procedure. First, every promoter of each set is used as input for the Match™ program (Kel et al., 2003), or any other similar program, which will predict TFBSs on it using a precompiled library of positional weight matrices (PWMs). The results, being the number of predicted TFBSs per PWM per promoter (further referred to as counts), are collected in the form of a matrix in which each row corresponds to a promoter sequence while the columns correspond to the used PWM. The columns are further referred to as PWM-vectors, characterizing a PWM by its number of predicted TFBSs per promoter. The choice for using the total number of predicted TFBSs per PWM per promoter is motivated by the observation of Papatsenko et al. (Papatsenko et al., 2002) that regulatory regions of Drosophila melanogaster contain multiple copies of robust motifs as well as weaker copies. In general, it is reasonable to assume that the presence of multiple binding sites for a transcription factor plays an important role. Moreover, it was shown in yeast that genes whose promoters share pairs of TFBSs are significantly more likely to be co-expressed than genes whose promoters have only single TFBSs in common (Pilpel et al., 2001). In line with this observation, the mere combination of single liver-specific TFBSs to yield composite enhancer elements yielded disappointing results (Lemken et al., 2005). As the DDM method considers both overrepresentation and association, considering multiple matches per promoter may help discover putative functional TFBSs by overrepresentation. Two TFBSs are considered correlated if their corresponding columns in the matrix are similar. Similarity between the columns can be measured using a distance function. With this approach, distance matrices summarizing all TFBS associations are constructed for the TFBSs in both sets of promoters. Finally, by calculating the DDM and performing multidimensional scaling (MDS) on this matrix to visualize its content in two dimensions, we can distinguish TFBSs that do not contribute to the observed differential gene expression, as they will be mapped near the origin of the DDM-MDS plot, from 'deviating'TFBSs that are likely responsible for the observed differential gene expression. As the MDS procedure will plot TFBSs that are strongly associated closer together than less associated ones, it highlights most of the otherwise often fuzzy interactions between TFBSs in the promoter datasets. Alternatively, results can be summarized in a table.

The rationale behind this procedure is based on association and individual overrepresentation (of one condition compared to the other). Indeed, although it is known that many transcription factors are specifically upregulated in the liver, this does not automatically imply that these are involved in upregulating gene expression in vivo. Important modules in one condition but not the other will be characterized by the overrepresentation of their consisting TFBSs and will be associated. This results in low DD values for two associated TFBSs, whereas the DD value for a TFBS that is overrepresented and common TFBSs will be high. Whether the TFBSs (and module) is typical for either the first or the second set of promoters can be derived from the sign of the column value sum of the original DDM.

The factors associated with the highest liver-specific gene expression (using very stringent conditions) are summarized in Table II:

TABLE II

Transcription factor binding sites associated with the highest liver-specific gene expression.

| Identifier | P-value | Q-value | Factor Name |
|---|---|---|---|
| V.LEF1_Q2 | 0.001 | 0.02 | LEF-1 |
| V.CEBP_Q2_01 | 0.008 | 0.03 | C/EBPalpha |

TABLE II-continued

Transcription factor binding sites associated with the highest liver-specific gene expression.

| Identifier | P-value | Q-value | Factor Name |
|---|---|---|---|
| V.HNF1_Q6_01 | 0.005 | 0.03 | HNF-1alpha |
| V.FOXO1_02 | 0.001 | 0.02 | FOXO1 |
| V.FOXO4_02 | 0.004 | 0.03 | FOXO4 |
| V.IRF1_Q6 | 0.005 | 0.03 | IRF-1 |
| V.E47_01 | 0.007 | 0.03 | E47 |
| V.E12_Q6 | 0.005 | 0.03 | E12 |

The P-value shown in Table II was determined using the DDM-MDS protocol, by calculating the distance between the origin of the MDS plot and the mapped TFBS. This distance quantifies the degree to which this TFBS is over-represented in the promoter data set. Next, a P value is estimated for this distance. The DDM-MDS procedure was applied to 10,000 random sets and the resultant distances from each mapped TFBS to the origin of the DDM-MDS plot were obtained. Subsequently, the P value of a real distance was calculated from the fraction of the corresponding 'background distances' exceeding this real distance.

The Q-value of an individual hypothesis test is the minimum 'False Discovery Rate' (FDR) at which the test may be called significant. FDR controls the expected proportion of incorrectly rejected null hypotheses (type I errors). For instance, a q-value of 0.02 (2%) means there is a 1 to 50 chance this result is a false positive.

The genomic context of the 59 upregulated genes was next searched for (cross-species) conserved regions enriched for TFBSs for the factors listed in Table II. Both up- and downstream sequences were taken into account. As the search was for binding sites conserved across multiple species, and for combinations of motifs rather than a single binding site; the likeliness that the identified sequences are actually involved in regulating gene expression increases. Indeed, it is well established that the mere presence or absence of transcription factor binding sites in a given promoter is not sufficient to confer high-level tissue specific expression. It is the combination of TFBSs as "regulons" within a particular chromosomal context that is key in dictating high-level tissue-specific expression. Of note, with the exception of E12 and E47 binding sites, according to DDM, the other TFBSs tend to form modules composed of different members (i.e. they are more 'associated' (lie closer together) in a DDM-MDS plot).

This approach led to the identification of 14 regulatory sequences enriched in the above transcription factor binding sites, summarized in Table III. These 14 sequences were then chosen for validation of their regulatory (enhancing) properties in vivo—see Examples 2 and 3.

TABLE III

Sequences identified enriched in the conserved transcription factor binding sites listed in table II.

| Sequence | Gene regulated by seq | Abbr. seq | Genomic location sequence | Length seq (bp) | Conserved TFBS present |
|---|---|---|---|---|---|
| SEQ ID NO: 1 | SERPINA1 | S1 | chr14: 93891375-93891462 | 88 | HNF1, CEBP, LEF-1/TCF |
| SEQ ID NO: 2 | SERPINA1 | S2 | chr14: 93897160-93897200 | 41 | HNF1, MyoD, Tal1β/E47 |
| SEQ ID NO: 3 | SERPINA1 | Serp | chr14: 93924743-93924814 | 72 | HNF1, FOX, CEBP, MyoD, LEF-1, LEF-1/TCF |
| SEQ ID NO: 4 | ApoC4 | A1 | chr19: 50131065-50131135 | 71 | FOX, CEBP, HNF-1 |
| SEQ ID NO: 5 | ApoH | A2 | chr17: 61560686-61560858 | 173 | IRF, HNF1, FOX, CEBP |
| SEQ ID NO: 6 | ApoH | A3 | chr17: 61597650-61598200 | 551 | CEBP, HNF1, LEF-1, LEF-1/TCF, FOX, Tal1β/E47, IRF |
| SEQ ID NO: 7 | ApoC1 | Apo | chr19: 50119497-50119590 | 94 | FOX, CEBP, LEF-1, LEF-1/TCF, MyoD, HNF1 |
| SEQ ID NO: 8 | ALB | AL | chr4: 74634950-74635050 | 101 | HNF1, CEBP, LEF-1, IRF, FOX |
| SEQ ID NO: 9 | AldoB | Aldo | chr9: 101277628-101277762 | 135 | CEBP, HNF1, IRF, FOX, LEF-1, LEF-1/TCF, MyoD |
| SEQ ID NO: 10 | CYP2E1 | C | chr10: 135229600-135229740 | 141 | CEBP, HNF1, LEF-1, LEF-1/TCF, MyoD, IRF, FOX |
| SEQ ID NO: 11 | FGA | F | chr4: 155869502-155869575 | 74 | CEBP, HNF1, LEF-1, LEF-1/TCF, MyoD |
| SEQ ID NO: 12 | HPR | H | chr16: 71063010-71063450 | 441 | CEBP, HNF1, LEF-1, LEF-1/TCF, FOX, Tal1β/E47, IRF, MyoD |
| SEQ ID NO: 13 | TF | T1 | chr3: 134944250-134944420 | 171 | CEBP, HNF1, LEF-1, LEF-1/TCF, FOX, Tal1β/E47, IRF, MyoD |
| SEQ ID NO: 14 | TTR | T2 | chr18: 27425669-27425838 | 170 | HNF1, CEBP, FOX, LEF-1, LEF-1/TCF, MyoD |

Abbr.: abbreviation,
seq: sequence.

Example 2

In Vivo Validation of Liver-Specific Regulatory Enhancer Sequences

Materials and Methods

Construction of pAAV-TTRmin-FIXIA

Normal mouse liver genomic DNA was first extracted using the DNAeasy Tissue kit, Qiagen, according to the manufacturer's instructions. The TTRminimal (TTRmin) promoter and part of the 5' UTR was subsequently amplified from this mouse liver genomic DNA using the following primers that were designed based on the Pubmed sequence (BC024702/M19524) of the 5' sequence of the transthyretin mouse gene.

```
Forward primer:
                                          (SEQ ID NO: 15)
AAGCGGCCGCGGTACCGTCTGTCTGCACATTTCGTAGAGCGAGTGTTC
(containing NotI & Acc65I restriction sites)

Reverse primer:
                                          (SEQ ID NO: 16)
AGCGCTAGCCAGGAGCTTGTGGATCTGTGTGACGGC
(containing NheI site)
```

The TTRmin promoter, devoid of the upstream enhancer sequences, has been described by Costa et al. (Costa et al., 1986, 1989). The start position of TTRmin lies at position -202 (relative to the Cap site), the sequence ends in the 5' untranslated region before the translational start site in TTR exon 1 (see SEQ ID NO: 17, see NCBI sequences BC024702 and M19524).

For PCR, the following components were added to an autoclaved microcentrifuge tube on ice: 10× AccuPrime Pfx Reaction mix (5.0 µl), primer mix (10 µM each, 1.5 µl), template DNA (100 ng), AccuPrime Pfx DNA Polymerase (2.5 units) and autoclaved, distilled water topped up to 50 µl. The template was denatured for 2 min at 95° C., followed by 35 cycles of PCR (denaturation: 95° C. for 15 s, annealing: 58° C. for 30 s, extension 68° C. for 1 min followed by a final extension of 68° C. for 5 min per kb. The resulting TTRmin sequence is included as SEQ ID NO: 17.

To obtain the pAAV-TTRmin-FIXIA plasmid, the PCR product was restricted with NotI and NheI and cloned into the corresponding Not I-Nhe I sites upstream of the factor IX minigene of pAAV-FIXIA. The FIX minigene (designated as FIXIA) is composed of the first exon of the human FIX cDNA followed by a truncated intron A and the rest of the FIX cDNA along with a truncated 70 bp 3'UTR, as described previously (Miao et al., 2001). The bovine growth hormone (GH) poly A was used as a transcription termination signal.

pAAV-FIXIA is a promoter-less construct derived from pAAV-ApoHCR-AAT-FIXIA. This pAAV-ApoHCR-AAT-FIXIA plasmid was described previously (VandenDriessche et al., 2007) and resembles the AAV-ApoHCR-AAT-FIX vector that was used previously in an AAV-based liver directed gene therapy trial for hemophilia B (Manno et al., 2006).

Construction of pAAV-ApoHCR-AAT-FIXIA

To generate the pAAV-plasmid used for control purposes, the pAAV-MCS plasmid (Stratagene, La Jolla, Calif., USA) was restricted with NotI and the pBS-HCRHP-FIXIA plasmid with SpeI. After filling in the cohesive ends with Klenow fragment, the two fragments were ligated by blunt-end ligation. pBS-HCRHP-FIXIA was kindly provided by Dr. C. Miao, University of Washington (Miao et al., 2001). As a shorter AAT promoter fragment targets expression to the liver with a greater specificity than that reported for larger AAT promoter fragments (Yull et al., 1995), the 347 bp short AAT promoter fragment was used to clone in our construct.

Enhancer Synthesis and Incorporation of Enhancers into pAAV-TTRmin-FIXIA

Figure 2:
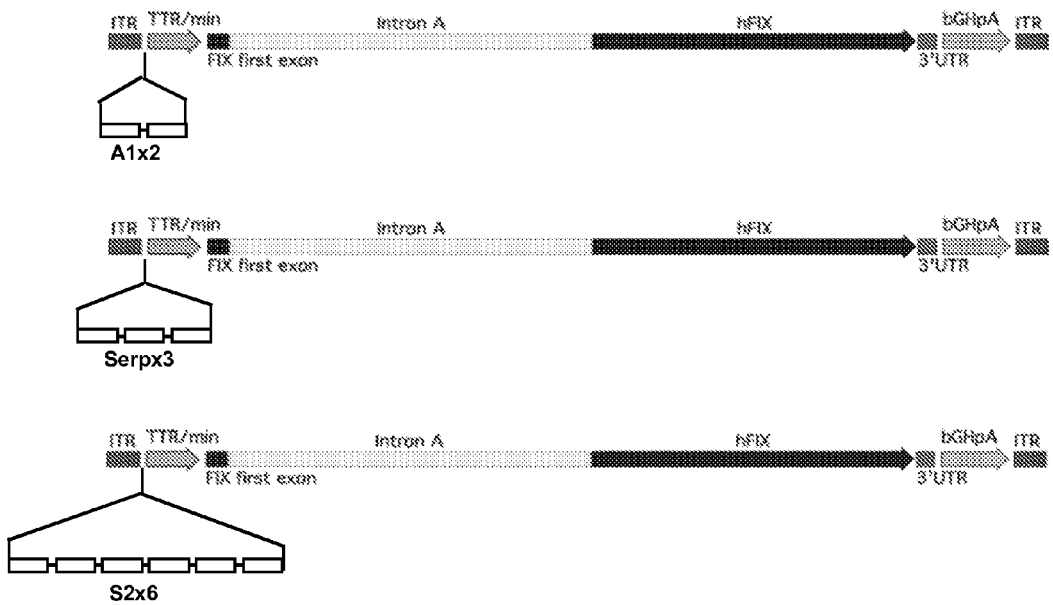
FIG. 2 is a schematic diagram of pAAV-TTRmin(E)n-FIXIA constructs containing liver-specific enhancer repeats upstream of the transthyretin minimal promoter. A1×2: two copies of the ApoC4 enhancer (SEQ ID NO: 4); Serpx3: three copies of the serpina1 enhancer 3 sequence (SEQ ID NO: 3); S2×6: six copies of the serpina1 enhancer 2 sequence (SEQ ID NO: 2). Other abbreviations are the same as in FIG. 1.

The enhancers (see Table III) were flanked with Acc65I and cloned upstream of the TTRmin after restriction of pAAV-TTRmin-FIXIA with Acc65I. AscI and MluI sites (isoschizomers) were built into the enhancer-containing fragment just after or before the Acc65I site to allow cloning of multiple enhancers upstream of the TTRmin. The regulatory elements flanked by these restriction sites are provided as SEQ IDs 18-31. This was accomplished after MluI restriction of the vector and ligation to the MluI/AscI restricted enhancer-containing fragment. A scheme of the resulting constructs is shown in FIG. 1. Additionally, for some of the enhancers (Serp (SEQ ID NO: 3), A1 (SEQ ID NO: 4), S2 (SEQ ID NO: 2)), multiple enhancer repeats were inserted upstream of the TTRmin promoter (as shown in FIG. 2). All resulting constructs were verified by DNA sequencing.

Hydrodynamic Gene Delivery

It is well established that the in vitro expression level of an expression construct in hepatic cell lines is not predictive of its in vivo performance. Instead, to directly assess the expression level of a given transgene in the liver, it is more appropriate to compare different expression cassettes by hydrodynamic hepatic gene delivery in vivo (Miao et al., 2000). Adult C57/Bl6 strains were used. Animal experiments were approved by the animal Ethical Commission of the K.U. Leuven. Animals were housed under Biosafety Level II conditions. Mice were injected by hydrodynamic gene delivery, as described (Liu et al., 1999). Briefly, mice were placed in a restraining holder and after heating the tail under an infrared lamp, different doses (0.5-1-2 µg) of the respective plasmids in a volume of 2 ml Dulbecco's phosphate buffered saline (equivalent to ten percent of the body weight of the mouse) was injected into the tail vein in a short time span of 5-7 seconds. This method has been shown to result in efficient in vivo transfection of liver cells. Endotoxin-free plasmid DNA was extracted using the Qiagen EndoFree kit (Hilden, Germany), according to the manufacturer's instructions. Blood was collected by retro-orbital bleeding under general anesthesia. The presence of human FIX in plasma samples with 20% 0.1 M sodium citrate (to prevent clotting) was determined using an enzyme-linked immunosorbant assay (Asserachrome FIX ELISA, Diagnostica Stago, Parsippany, N.J., USA). Each cohort included 5 mice per dose per vector.

Results

Figure 3:
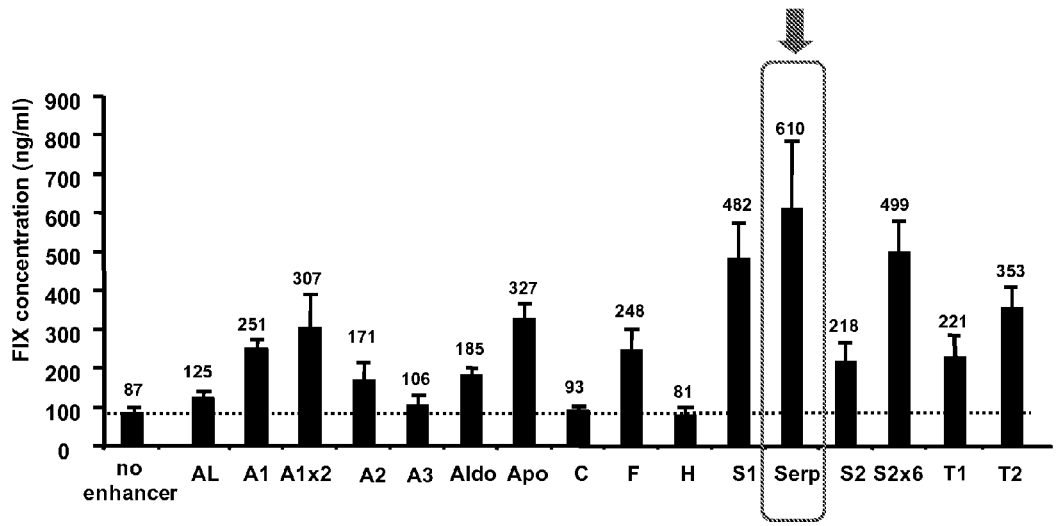
FIG. 3 details the in vivo validation of hepatocyte-specific enhancers. Expression of Factor IX (FIX) was determined using a human FIX-specific ELISA 2 days post-transfection following hydrodynamic gene delivery of 2 µg of plasmid DNA in adult C57Bl/6 mice. For abbreviations of enhancers, see Table III. Serp enhancer (SEQ ID NO: 3) indicated with arrow.

To assess the effect of the in silico identified hepatocyte-specific regulatory enhancer elements on in vivo expression, expression constructs expressing hFIX were transfected into hepatocytes by hydrodynamic gene delivery (2 µg DNA). In these constructs, hFIX expression was driven by the TTRmin promoter or by the TTRmin promoter in conjunction with evolutionary conserved hepatocyte-specific enhancer(s) that are highly enriched in TFBS, identified by the DDM algorithm and multidimensional scaling method. The results shown in FIG. 3 indicate that the majority of the enhancers tested (AL, A1, A2, Aldo, Apo, F, S1, Serp, S2, T1 and T2) resulted in a significant increase (>40%) in hFIX expression levels in the plasma of recipient mice, compared to the levels obtained when the TTRmin promoter was used to drive hFIX expression (FIG. 3). Hence, nearly 80% of the enhancers tested (11/14) resulted in significantly improved hFIX expression levels which further validates the DDM prediction algorithm. Remarkably, especially the shorter sequences identified are efficient in increasing expression: the two sequences longer than 400 nucleotides tested (A3, H) did not yield significantly increased FIX levels in this experiment. This does however not exclude a physiological role for these sequences. The highest FIX levels were achieved following in vivo hepatic transfection with the pAAV-TTRmSerp-FIXIA construct. These levels were increased 7-fold compared to when the TTRmin promoter was used. Of note, factor IX expression was limited to the liver for all constructs, no 'leakage' of expression (e.g. in the spleen) was observed.

Example 3

Figure 4:
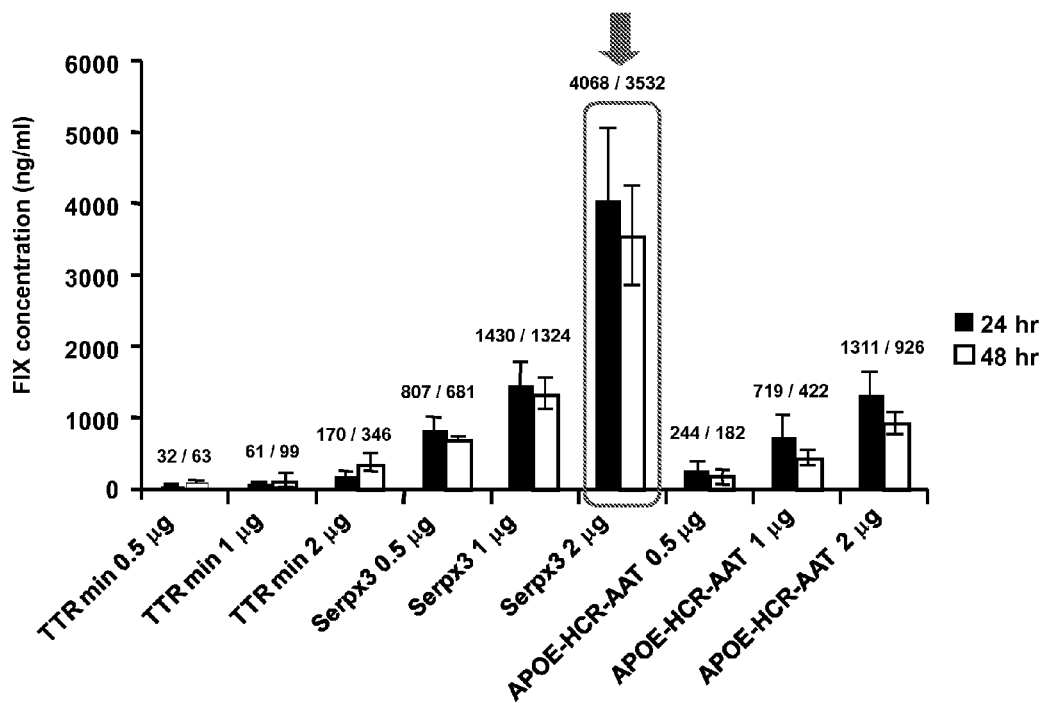
FIG. 4 shows the in vivo validation of triplet repeat serpina1 enhancer 3 (SEQ ID NO: 3) sequences. Expression of Factor IX (FIX) was determined using a human FIX-specific ELISA 24 or 48 hr post-transfection following hydrodynamic gene delivery of 0.5, 1 or 2 μg (as indicated) of plasmid DNA in adult C57Bl/6 mice. TTR min: construct with the transthyretin minimal promoter without enhancer; Serpx3: construct with triplet repeat serpina1 enhancer 3 (SEQ ID NO: 3) sequences as shown in FIG. 2; ApoE-HCR-AAT: construct combining the ApoE enhancer and AAT promoter, as previously described (Miao et al., 2000).

In Vivo Validation of Modules of Several Liver-Specific Regulatory Enhancer Sequences To further validate the potency of these enhancers/regulatory elements, multiple enhancer repeats were incorporated upstream of the TTRmin promoter (e.g. A1: repeated 2×, S2: repeated 6× or Serp: repeated 3×, see FIG. 2). The results show that incorporation of multiple enhancers resulted in an additional increase in circulating hFIX levels (FIGS. 3 & 4). Indeed, the highest FIX levels were achieved following in vivo hepatic transfection with the pAAV-TTRmSerp3-FIXIA construct that contained a triple repeat of the Serp3 enhancer (FIG. 4). This was confirmed at all doses tested (0.5-1-2 µg DNA). The FIX levels obtained with that construct are about 20 to 25-fold higher than the levels obtained with the pAAV-TTRmin-FIX construct and significantly higher than those obtained with one of the most robust hepatocyte-specific expression cassettes known (i.e. pAAV-Apo-HCR-AAT-FIX) (FIG. 4). Using only 2 µg of DNA, near-physiologic FIX levels could be obtained (normal FIX levels: 5000 ng/ml=100%). Of note, the FIX concentrations obtained with the pAAV-Apo-HCR-AAT-FIX plasmid are in good agreement with earlier reported concentrations of between 10 and 40% of physiologic FIX levels with this construct (Miao et al., 2000), demonstrating the reliability of the data. Collectively, these results demonstrate that the de novo generation of hepatocyte-specific promoter/enhancers resulted in robust FIX expression levels and hereby confirms the superiority of the enhancer-modified constructs.

Example 4

Further Combinations of Regulatory Elements

The enhancers are further validated by making different combinations of the enhancers rather than using several copies of the same enhancer. Both combinations using enhancers with similar transcription factor binding sites as combinations using enhancers with complementary TFBS are tested in combination with the TTR minimal promoter.

Further combinations are made with parts of the identified regulatory elements, e.g. using only certain regions of SEQ IDs 1-14, in particular those regions with transcription factor binding sites, although not necessarily limited thereto. In doing so, new, even more powerful regulatory/enhancing sequences may be obtained.

Example 5

In Vivo Validation of Liver-Specific Regulatory Enhancer Sequences Via AAV Vector Gene Delivery Materials and Methods
Cell Lines and Culture Conditions Cells were cultured in Dulbecco's modified Eagle's medium (DMEM) supplemented with 2 mM L-glutamine (Gln), 100 IU/ml penicillin, 100 µg/ml streptomycin and 10% heat-inactivated fetal bovine serum (FBS, Invitrogen, Merelbeke, Belgium).

AAV Vector Production: AAV9-TTRminSerp-FIXIA.

AAV-based vectors were generated that express Factor IX from the same hepatocyte-specific expression constructs as in Example 2 (pAAV-TTRmin-FIXIA). In particular, the construct with incorporation of the enhancer Serp (SEQ ID NO: 3, see Table III) was used for packaging into AAV viral vectors. As an example, the AAV serotype 9 viral vector was chosen to package the construct, known to be a promising vector for gene therapy (Vandendriessche et al. 2007), yielding AAV9-TTRminSerp-FIXIA. AAV vectors expressing human FIX were produced at high-titer by calcium phosphate transfection according to the manufacturer's instruction (Calcium phosphate transfection kit, Invitrogen) of 293 cells with AAV2-vector DNA (26 µg/10 cm dish), an adenoviral helper plasmid (52 µg/10 cm dish) and AAV helper plasmids expressing $Rep_2$ and $Cap_9$ (26 µg/10 cm dish) for production of AAV9 serotypes, as described in Gao et al. (2002), Mingozzi et al. (2003) and Gehrke (2003).

Two days post-transfection, cells were lysed by successive freeze-thaw cycles and sonication. Lysates were treated with benzonase (Merck) and deoxycholate (Sigma-Aldrich) and subsequently subjected to three successive rounds of cesium chloride density ultracentrifugation. The fractions containing the AAV particles were concentrated using an Amicon filter (Millipore) and washed with PBS 1 mM $MgCl_2$. Vector genome titers were determined by quantitative polymerase chain reaction (qPCR) using Taq Man® probes and primers specific for the human factor FIX (hFIX) cDNA sequence (forward [exons] 5'AGGGATATCGACTTGCAGAAAA (SEQ ID NO: 32), probe [exons-exon6]: 5'AGTCCTGTGAACCAGCAGTGCCATTTC (SEQ ID NO: 33), reverse-exon6: 5'GTGAGCTTAGAAGTTTGTGAAACAG (SEQ ID NO: 34)) or the polyadenylation signal (forward: 5'GCCTTCTAGTTGCCAGCCAT (SEQ ID NO: 35), probe: 5'TGTTTGCCCCTCCCCCGTGC (SEQ ID NO: 36), reverse: 5'GGCACCTTCCAGGGTCAAG (SEQ ID NO: 37)).

Animal Studies

Animal procedures were approved by the animal Ethical Commission of the K.U. Leuven. Animals were housed under Biosafety Level II conditions. Mice were injected with the AAV9-TTRmin-FIXIA or AAV9-TTRminSerp-FIXIA vector as described in Vandendriessche et al. (2007). Briefly, $3 \times 10^9$ or $3 \times 10^{12}$ AAV vector genomes (vg) were injected (i.v.) into the tail vein of adult C57Bl6 mice (2-5 mice/group). Blood was collected by retro-orbital bleeds under general anesthesia. Human FIX expression was determined in citrated mouse plasma using a human FIX-specific ELISA (Asserachrome/Diagnostica Stago, Parsippany, N.J., USA).

Human FIX mRNA levels were analyzed in total RNA, isolated from different organs by a silica-membrane based purification kit (Invitrogen). Briefly, 2 µg of total RNA from each sample was subjected to reverse-transcription using a cDNA synthesis kit (Invitrogen); subsequently a cDNA amount corresponding to 20 ng of total RNA was amplified by (Q)PCR using FIX primers described above. The hFIX mRNA levels were normalized to mRNA levels of the murine glyceraldehyde-3-phosphate dehydrogenase (GAPDH) gene using TaqMan® probes and primers (forward: TGTGTCCGTCGTGGATCTGA (SEQ ID NO: 38), probe CCTGGAGAAACCTGCCAAGTATGATGACA (SEQ ID NO: 39), reverse CCTGCTTCACCACCTTCTTGA (SEQ ID NO: 40)). RNA samples were amplified with and without RT to exclude genomic DNA amplification. The size of the amplified PCR fragment was verified on a 1.5% agarose gel.

Results

In the previous examples, the DNA was delivered to the liver by high-pressure naked DNA gene delivery (hydrodynamic transfection), without relying on viral vectors. Here, the pAAV-TTRmin-FIXIA and pAAV-TTRminSerp-FIXIA constructs were packaged into AAV viral vectors. These vectors can directly transfer genes into liver without having to resort to high-pressure hydrodynamic transfections. AAV gene delivery into liver is a clinically relevant approach, they are devoid of viral genes and have the potential for long-term gene expression. As an example AAV serotype 9 was used (Vandendriessche et al. 2007).

Figure 5:
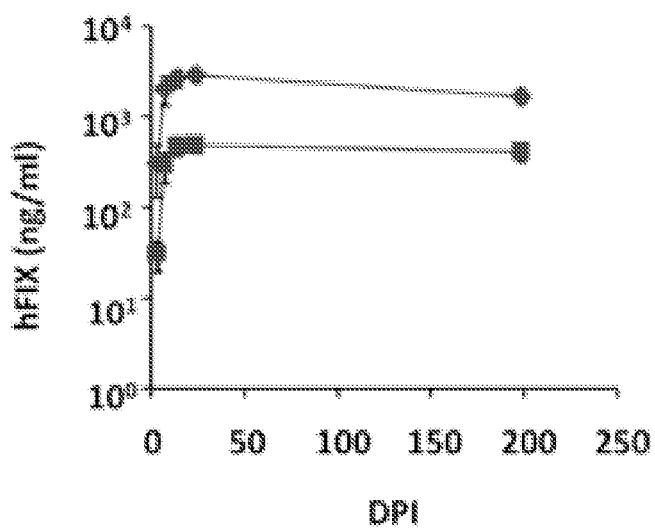
FIG. 5 shows FIX expression after intravenous injection of AAV9-TTRminSerp-FIXIA (circles) mice and AAV9-TTRmin-FIXIA (squares) in C57/Bl6 mice (n=3-5). hFIX expression levels were determined by ELISA on citrated plasma collected at different time intervals (dpi: days post infection).

The superior performance of the Serp enhancer (SEQ ID NO: 3, see Table III) was confirmed following hepatic transduction with AAV9 vectors. In particular, AAV9-TTRmin-FIXIA and AAV9-TTRminSerp-FIXIA vectors were injected intravenously by tail vein injection into adult C57Bl/6 mice at a dose of $5\times10^9$ genome copies (gc)/mouse. The results shown in FIG. 5 indicate that the incorporation of the Serp enhancer led to a robust increase in FIX expression levels. The increase in FIX protein levels after inclusion of the Serp enhancer in the AAV9 vector was also consistent with a 10-fold increase in relative FIX mRNA levels when comparing AAV9-TTRmin-FIXIA with AAV9-TTRminSerp-FIXIA. Remarkably, the AAV9-TTRminSerp-FIXIA vector reached sustained therapeutic FIX levels at a relatively low dose (>30% of normal FIX levels at $5\times10^9$ gc/mouse after 200 days), which underscores its potency.

Figure 6:
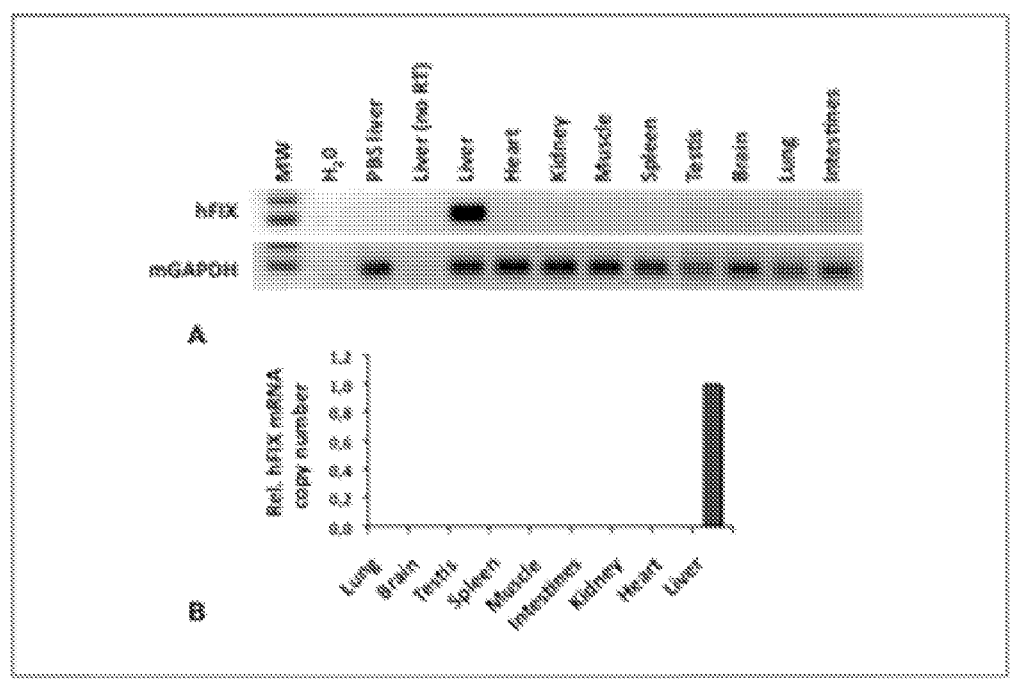
FIG. 6 shows that human FIX (hFIX) mRNA expression is exclusively restricted to the liver, whereas the FIX gene was not expressed in any other tissue (upon injection with $3 \times 10^{12}$ vector genomes). A. RT-qPCR on total RNA from different organs of AAV9-TTRminSerp-FIXIA injected mice. The murine glyceraldehyde-3-phosphate dehydrogenase (mGAPDH) housekeeping gene is used as a control for quantitative gene expression. B. Relative hFIX mRNA copy number in different organs determined by RT-qPCR (relative to hFIX mRNA copy number in liver).

Further, it was demonstrated by RT-qPCR on total RNA from different organs of AAV9-TTRminSerp-FIXIA injected mice, that hFIX mRNA expression is exclusively restricted to the liver whereas the FIX gene was not expressed in any other tissue (FIG. 6). This was confirmed even when extremely high vector doses of $3\times10^{12}$ genome copies (gc) were injected per mouse (which assures gene delivery in other tissues), resulting in exceptionally high FIX levels (>10000%, i.e. more than 500,000 ng/ml of normal hFIX levels, which are defined as 100% or 5,000 ng/ml). Yet, FIX mRNA is only expressed in the liver, which confirms the tissue-specificity of the expression.

References

Ausubel et al., Current Protocols in Molecular Biology (Supplement 47), John Wiley & Sons, New York (1999).

Barajas M, Mazzolini G, Genové G, Bilbao R, Narvaiza I, Schmitz V, Sangro B, Melero I, Qian C, Prieto J. Gene therapy of orthotopic hepatocellular carcinoma in rats using adenovirus coding for interleukin 12. Hepatology. 2001 January; 33(1):52-61.

Berger S L, Kimmel A R. Guide to Molecular Cloning Techniques. Methods in Enzymology, vol. 152, Academic Press, Inc., San Diego, Calif., 1987.

Brown B D, Venneri M A, Zingale A, Sergi L, Naldini L. Endogenous microRNA regulation suppresses transgene expression in hematopoietic lineages and enables stable gene transfer. Nat Med. 2006 May; 12(5):585-91.

Brown B D, Cantore A, Annoni A, Sergi L S, Lombardo A, Della Valle P, D'Angelo A, Naldini L. A microRNA-regulated lentiviral vector mediates stable correction of hemophilia B mice. Blood. 2007 Dec. 15; 110(13):4144-52.

Budker V, Zhang G, Knechtle S, Wolff J A. Naked DNA delivered intraportally expresses efficiently in hepatocytes. Gene Ther. 1996 July; 3(7):593-8.

Chowdhury J R, Grossman M, Gupta S, Chowdhury N R, Baker J R Jr, Wilson J M. Long-term improvement of hypercholesterolemia after ex vivo gene therapy in LDLR-deficient rabbits. Science. 1991 Dec. 20; 254 (5039):1802-5.

Costa R H, Lai E, Darnell J E Jr. Transcriptional control of the mouse prealbumin (transthyretin) gene: both promoter sequences and a distinct enhancer are cell specific. Mol Cell Biol. 1986 December; 6(12):4697-708.

Costa R H, Grayson D R, Darnell J E Jr. Multiple hepatocyte-enriched nuclear factors function in the regulation of transthyretin and alpha 1-antitrypsin genes. Mol Cell Biol. 1989 April; 9(4):1415-25.

Cristiano R J, Smith L C, Kay M A, Brinkley B R, Woo S L. Hepatic gene therapy: efficient gene delivery and expression in primary hepatocytes utilizing a conjugated adenovirus-DNA complex. Proc Natl Acad Sci USA. 1993 Dec. 15; 90(24):11548-52.

De Bleser P, Hooghe B, Vlieghe D, van Roy F. A distance difference matrix approach to identifying transcription factors that regulate differential gene expression. Genome Biol. 2007; 8(5):R83.

Ferry N, Heard J M. Liver-directed gene transfer vectors. Hum Gene Ther. 1998 Sep. 20; 9(14):1975-81.

Follenzi A, Sabatino G, Lombardo A, Boccaccio C, Naldini L. Efficient gene delivery and targeted expression to hepatocytes in vivo by improved lentiviral vectors. Hum Gene Ther. 2002 Jan. 20; 13(2):243-60.

Gao G P, Alvira M R, Wang L, Calcedo R, Johnston J, Wilson J M. Novel adeno-associated viruses from rhesus monkeys as vectors for human gene therapy. Proc Natl Acad Sci 2002; 99: 11854-9

Mingozzi F, Liu Y L, Dobrzynski E, Kaufhold A, Liu J H, Wang Y, Arruda V R, High K A, Herzog R W. Induction of immune tolerance to coagulation factor IX antigen by in vivo hepatic gene transfer. J Clin Invest 2003; 111: 1347-56.

Gehrke S, Jérôme V, Müller R. Chimeric transcriptional control units for improved liver-specific transgene expression. Gene. 2003 Dec. 11; 322:137-43.

Ghosh S S, Takahashi M, Thummala N R, Parashar B, Chowdhury N R, Chowdhury J R. Liver-directed gene therapy: promises, problems and prospects at the turn of the century. J. Hepatol. 2000; 32(1 Suppl):238-52.

Jenke A C, Stehle I M, Herrmann F, Eisenberger T, Baiker A, Bode J, Fackelmayer F O, Lipps H J. Nuclear scaffold/matrix attached region modules linked to a transcription unit are sufficient for replication and maintenance of a mammalian episome. Proc Natl Acad Sci USA. 2004 Aug. 3; 101(31):11322-7.

Kay M A, Baley P, Rothenberg S, Leland F, Fleming L, Ponder K P, Liu T, Finegold M, Darlington G, Pokorny W, Woo S L C. Expression of human alpha 1-antitrypsin in dogs after autologous transplantation of retroviral transduced hepatocytes. Proc Natl Acad Sci USA. 1992 Jan. 1; 89(1):89-93.

Kel A E, Gossling E, Reuter I, Cheremushkin E, Kel-Margoulis O V, Wingender E. MATCH: A tool for searching transcription factor binding sites in DNA sequences. Nucleic Acids Res. 2003 Jul. 1; 31(13):3576-9.

Kistner A, Gossen M, Zimmermann F, Jerecic J, Ullmer C, Lubbert H, Bujard H. Doxycycline-mediated quantitative and tissue-specific control of gene expression in transgenic mice. Proc Natl Acad Sci USA. 1996 Oct. 1; 93(20):10933-8.

Kramer M G, Barajas M, Razquin N, Berraondo P, Rodrigo M, Wu C, Qian C, Fortes P, Prieto J. In vitro and in vivo comparative study of chimeric liver-specific promoters. Mol Ther. 2003 March; 7(3):375-85.

Kuriyama S, Yoshikawa M, Ishizaka S, Tsujii T, Ikenaka K, Kagawa T, Morita N, Mikoshiba K. A potential approach for gene therapy targeting hepatoma using a liver-specific promoter on a retroviral vector. Cell Struct Funct. 1991 December; 16(6):503-10.

Le M, Okuyama T, Cai S R, Kennedy S C, Bowling W M, Flye M W, Ponder K P. Therapeutic levels of functional human factor X in rats after retroviral-mediated hepatic gene therapy. Blood. 1997 Feb. 15; 89(4):1254-9.

Lemken M L, Wybranietz W A, Schmidt U, Graepler F, Armeanu S, Bitzer M, Lauer U M. Expression liver-directed genes by employing synthetic transcriptional control units. World J. Gastroenterol. 2005 Sep. 14; 11(34):5295-302.

Liu F, Song Y, Liu D. Hydrodynamics-based transfection in animals by systemic administration of plasmid DNA. Gene Ther. 1999 July; 6(7):1258-66.

Manno C S, Pierce G F, Arruda V R, Glader B, Ragni M, Rasko J J, Ozelo M C, Hoots K, Blatt P, Konkle B, Dake M, Kaye R, Razavi M, Zajko A, Zehnder J, Rustagi P K, Nakai H, Chew A, Leonard D, Wright J F, Lessard R R, Sommer J M, Tigges M, Sabatino D, Luk A, Jiang H, Mingozzi F, Couto L, Ertl H C, High K A, Kay M A. Successful transduction of liver in hemophilia by AAV-Factor IX and limitations imposed by the host immune response. Nat Med. 2006 March; 12(3):342-7.

Manzini S, Vargiolu A, Stehle I M, Bacci M L, Cerrito M G, Giovannoni R, Zannoni A, Bianco M R, Formi M, Donini P, Papa M, Lipps H J, Lavitrano M. Genetically modified pigs produced with a nonviral episomal vector. Proc Natl Acad Sci USA. 2006 Nov. 21; 103(47):17672-7.

Miao C H, Ohashi K, Patijn G A, Meuse L, Ye X, Thompson A R, Kay M A. Inclusion of the hepatic locus control region, an intron, and untranslated region increases and stabilizes hepatic factor IX gene expression in vivo but not in vitro. Mol Ther. 2000 June; 1(6):522-32

Miao C H, Thompson A R, Loeb K, Ye X. Long-term and therapeutic-level hepatic gene expression of human factor IX after naked plasmid transfer in vivo. Mol Ther. 2001 June; 3(6):947-57

Miller A D. Retrovirus packaging cells. Hum Gene Ther. 1990 Spring; 1(1):5-14.

Naldini L, Blömer U, Gallay P, Ory D, Mulligan R, Gage F H, Verma I M, Trono D. In vivo gene delivery and stable transduction of nondividing cells by a lentiviral vector. Science. 1996 Apr. 12; 272(5259):263-7.

Papatsenko D A, Makeev V J, Lifanov A P, Regnier M, Nazina A G, Desplan C. Extraction of functional binding sites from unique regulatory regions: the Drosophila early developmental enhancers. Genome Res. 2002 March; 12(3):470-81.

Pastore L, Morral N, Zhou H, Garcia R, Parks R J, Kochanek S, Graham F L, Lee B, Beaudet A L. Use of a liver-specific promoter reduces immune response to the transgene in adenoviral vectors. Hum Gene Ther. 1999 Jul. 20; 10(11):1773-81.

Pilpel Y, Sudarsanam P, Church G M. Identifying regulatory networks by combinatorial analysis of promoter elements. Nat Genet. 2001 October; 29(2):153-9.

Prieto J, Herraiz M, Sangro B, Qian C, Mazzolini G, Melero I, Ruiz J. The promise of gene therapy in gastrointestinal and liver diseases. Gut 2003; 52(Suppl II):ii49-ii54.

Sambrook et al., Molecular Cloning: A Laboratory Manual, $2^{nd}$ ed., Cold Spring Harbor Press, Plainsview, N.Y. (1989).

Schagen F H, Ossevoort M, Toes R E, Hoeben R C. Immune responses against adenoviral vectors and their transgene products: a review of strategies for evasion. Crit Rev Oncol Hematol. 2004 April; 50(1):51-70.

Shen R F, Clift S M, DeMayo J L, Sifers R N, Finegold M J, Woo S L. Tissue-specific regulation of human alpha 1-antitrypsin gene expression in transgenic mice. DNA. 1989 March; 8(2):101-8.

Simonet W S, Bucay N, Lauer S J, Taylor J M. A far-downstream hepatocyte-specific control region directs expression of the linked human apolipoprotein E and C-I genes in transgenic mice. J Biol Chem. 1993 Apr. 15; 268(11):8221-9.

Snyder R O, Miao C, Meuse L, Tubb J, Donahue B A, Lin H F, Stafford D W, Patel S, Thompson A R, Nichols T, Read M S, Bellinger D A, Brinkhous K M, Kay M A. Correction of hemophilia B in canine and murine models using recombinant adeno-associated viral vectors. Nat Med. 1999 January; 5(1):64-70.

Tenenbaum L, Lehtonen E, Monahan P E. Evaluation of risks related to the use of adeno-associated virus-based vectors. Curr Gene Ther 2003; 3: 545-565.

Trapnell B C. Adenoviral vectors for gene transfer. Adv. Drug Del. Rev. 1993 12: 185-199.

VandenDriessche T, Thorrez L, Naldini L, Follenzi A, Moons L, Berneman Z, Cohen D, Chuah M K. Lentiviral vectors containing the human immunodeficiency virus type-1 central polypurine tract can efficiently transduce nondividing hepatocytes and antigen-presenting cells in vivo. Blood. 2002 Aug. 1; 100(3):813-22.

VandenDriessche T, Thorrez L, Acosta-Sanchez A, Petrus I, Wang L, Ma L, De Waele L, Iwasaki Y, Gillijns V, Wilson J M, Collen D, Chuah M K. Efficacy and safety of adeno-associated viral vectors based on serotype 8 and 9 vs. lentiviral vectors for hemophilia B gene therapy. J Thromb Haemost. 2007 January; 5(1):16-24.

Villa E, Grottola A, Buttafoco P, Colantoni A, Bagni A, Ferretti I, Cremonini C, Bertani H, Manenti F. High doses of alpha-interferon are required in chronic hepatitis due to coinfection with hepatitis B virus and hepatitis C virus: long term results of a prospective randomized trial. Am J Gastroenterol. 2001 October; 96(10):2973-7.

Wood M, Perrotte P, Onishi E, Harper M E, Dinney C, Pagliaro L, Wilson D R. Biodistribution of an adenoviral vector carrying the luciferase reporter gene following intravesical or intravenous administration to a mouse. Cancer Gene Ther. 1999 July-August; 6(4):367-72.

Xia D, Zhang M M, Yan L N. Recent advances in liver-directed gene transfer vectors. Hepatobiliary Pancreat Dis Int. 2004 August; 3(3):332-6.

Yamada T, Iwasaki Y, Tada H, Iwabuki H, Chuah M K, VandenDriessche T, Fukuda H, Kondo A, Ueda M, Seno M, Tanizawa K, Kuroda S. Nanoparticles for the delivery of genes and drugs to human hepatocytes. Nat Biotechnol. 2003 August; 21(8):885-90.

Yull F E, Wallace R M, Clark A J. Restricted tissue-specific but correct developmental expression mediated by a short human alpha 1AT promoter fragment in transgenic mice. Transgenic Res. 1995 January; 4(1):70-4.

Zhang G, Budker V, Wolff J A. High levels of foreign gene expression in hepatocytes after tail vein injections of naked plasmid DNA. Hum Gene Ther. 1999 Jul. 1; 10(10):1735-7.

The invention claimed is:

1. A nucleic acid expression cassette comprising an isolated nucleic acid regulatory element of 150 nucleotides or less for enhancing liver-specific gene expression, wherein the nucleic acid regulatory element comprises a polynucleotide selected from the group consisting of: SEQ ID NO: 1, SEQ ID NO: 2, SEQ ID NO: 4, SEQ ID NO: 8, SEQ ID NO: 9, SEQ ID NO: 10, SEQ ID NO: 11, and a polynucleotide having 95% identity to any of these sequences, wherein the nucleic acid regulatory element is operably linked to a promoter and a heterologous transgene.

2. The nucleic acid expression cassette of claim 1, wherein the polynucleotide is selected from the group consisting of SEQ ID NO: 1, SEQ ID NO: 2, and a sequence having 95% identity to any of these sequences.

3. The nucleic acid expression cassette of claim 1, comprising two or more isolated nucleic acid regulatory elements, wherein each of the nucleic acid regulatory elements comprise:
a polynucleotide selected from the group consisting of: SEQ ID NO: 1, SEQ ID NO: 2, SEQ ID NO: 4, SEQ ID NO: 8, SEQ ID NO: 9, SEQ ID NO: 10, SEQ ID NO: 11, and a polynucleotide having 95% identity to any of these sequences.

4. The nucleic acid expression cassette of claim 3, wherein the two or more isolated nucleic acid regulatory elements are identical.

5. The nucleic acid expression cassette according to claim 1, wherein the promoter is a liver-specific promoter.

6. The nucleic acid expression cassette according to claim 5, wherein the promoter is from the transthyretin (TTR) gene.

7. The nucleic acid expression cassette according to claim 1, wherein the promoter is a minimal promoter.

8. The nucleic acid expression cassette according to claim 1, wherein the heterologous transgene encodes a therapeutic protein.

9. The nucleic acid expression cassette according to claim 8, wherein the therapeutic protein is a clotting factor.

10. The nucleic acid expression cassette according to claim 9, wherein the therapeutic protein is factor IX.

11. A method for expressing a protein in a liver cell, the method comprising:
introducing into the liver cell the nucleic acid expression cassette according to claim 3; and
expressing the heterologous transgene protein product thereof in the liver cell.

12. A method of gene therapy for a subject in need thereof, the method comprising:
introducing into the subject's liver a nucleic acid expression cassette according to claim 8; and
expressing a therapeutic amount of the protein in the liver.

13. The method according to claim 12, wherein the therapeutic protein is a clotting factor.

14. A nucleic acid expression cassette comprising:
an isolated nucleic acid regulatory element of 150 nucleotides or less consisting of a polynucleotide selected from the group consisting of SEQ ID NO: 1, SEQ ID NO: 2, SEQ ID NO: 3, SEQ ID NO: 4, SEQ ID NO: 7, SEQ ID NO: 8, SEQ ID NO: 9, SEQ ID NO: 10, and SEQ ID NO: 11;
a promoter, and
a heterologous transgene encoding a clotting factor,
wherein the polynucleotide is operably linked to the promoter and the heterologous transgene.

15. A vector comprising an isolated nucleic acid regulatory element of 150 nucleotides or less for enhancing liver-specific gene expression, wherein the nucleic acid regulatory element comprises a polynucleotide selected from the group consisting of SEQ ID NO: 1, SEQ ID NO: 2, SEQ ID NO: 4, SEQ ID NO: 8, SEQ ID NO: 9, SEQ ID NO: 10, SEQ ID NO: 11, and a polynucleotide having 95% identity to any of these polynucleotides;
a promoter, and
a heterologous transgene,
wherein the polynucleotide is operably linked to the promoter and the heterologous transgene.

16. The vector according to claim 15, wherein the vector is a viral vector, a lentiviral vector, or an adeno associated virus AAV vector.

17. A nucleic acid expression vector consisting of:
a promoter operably linked to a gene of interest, wherein the gene of interest comprises a heterologous transgene;
one or more polyadenylation sequences; and
a nucleic acid regulatory element,
wherein the nucleic acid regulatory element comprises 150 or fewer nucleotides and enhances liver-specific expression of the gene of interest, and wherein the nucleic acid regulatory element consists of a polynucleotide selected from the group consisting of SEQ ID NO: 3, SEQ ID NO: 1, SEQ ID NO: 2, SEQ ID NO: 4, SEQ ID NO: 7, SEQ ID NO: 8, SEQ ID NO: 9, SEQ ID NO: 10, and SEQ ID NO: 11.

18. The nucleic acid expression cassette of claim 1, wherein the isolated nucleic acid regulatory element is isolated from its endogenous promoter.

* * * * *

SEQUENCE LISTING

<160> NUMBER OF SEQ ID NOS: 40

<210> SEQ ID NO 1
<211> LENGTH: 88
<212> TYPE: DNA
<213> ORGANISM: Homo sapiens

<400> SEQUENCE: 1
ggagttgctg gtgcttcccc aggctggaga ttgagttaat attaacaggc ccaaggcgat    60
gtgggcttgt gcaatcatag gcccggcc                                      88

<210> SEQ ID NO 2
<211> LENGTH: 41
<212> TYPE: DNA
<213> ORGANISM: Homo sapiens

<400> SEQUENCE: 2
atcgccaggt cacctgagga gttaatgaat acatatctcc t                       41

<210> SEQ ID NO 3
<211> LENGTH: 72
<212> TYPE: DNA
<213> ORGANISM: Homo sapiens

<400> SEQUENCE: 3
gggggaggct gctggtgaat attaaccaag gtcaccccag ttatcggagg agcaaacagg    60
ggctaagtcc ac                                                       72

<210> SEQ ID NO 4
<211> LENGTH: 71
<212> TYPE: DNA
<213> ORGANISM: Homo sapiens

<400> SEQUENCE: 4
tgaatgacct tcagcctgtt cccgtccctg atatgggcaa acattgcaag cagcaaacag    60
caaacacata g                                                        71

<210> SEQ ID NO 5
<211> LENGTH: 173
<212> TYPE: DNA
<213> ORGANISM: Homo sapiens

<400> SEQUENCE: 5
ggcgtattct taagaataga ttaaataatc ataaaaagat ctatacttaa aaattgaaaa    60
atgcttaaat attaaaattc ttctcataaa aaaatactaa tttaaaaatg agcctgaaat   120
gtttatctat ttattgcaca gggttgcata cataaaacga cacaccctct tgt          173

<210> SEQ ID NO 6
<211> LENGTH: 551
<212> TYPE: DNA
<213> ORGANISM: Homo sapiens

<400> SEQUENCE: 6
agtttggaac aagactatat accatatcct acaggaagaa taaaagtaaa ggaaaggtgc    60
catctctact gaatagagag tcctaacaaa aaggcttcaa aaggactctg catctttaat   120
aatataaaaa ggctaggaca caaacagcat catctaaaat gccattagaa atacttcaca   180
tacaaaaagg tctaagtaaa gcaggatttt ataaagtgat caaaaagaa acactaaggg    240 ggaaaaatct tttaagatta aagaggtttt tcaaggaca agttgaagtg gctgtaaaat   300

-continued

```
ttatgaggca gcattaaact tcagttctaa gtaacaataa attattcacc ataaaaacat      360
acatgtgtca aatattataa gcctcttaaa cttttaaaa caatttcttg cagaactgat      420
tagatatatt aagtcaagat tagcagatac taacttttc attagcatac tatgatcact      480
cagagtaaag gaggaaattt agaaaagaaa taagacagaa ccatcaatag tcgattcacc      540
accaaatgtg a                                                          551
```

<210> SEQ ID NO 7
<211> LENGTH: 94
<212> TYPE: DNA
<213> ORGANISM: Homo sapiens

<400> SEQUENCE: 7

```
ctaaaatggg caaacattgc aagcagcaaa cagcaaacac acagccctcc ctgcctgctg       60
accttggagc tggggcagag gtcagagacc tctc                                 94
```

<210> SEQ ID NO 8
<211> LENGTH: 101
<212> TYPE: DNA
<213> ORGANISM: Homo sapiens

<400> SEQUENCE: 8

```
cagccaatga aatacaaaga tgagtctagt taataatcta caattattgg ttaaagaagt       60
atattagtgc taatttccct ccgtttgtcc tagcttttct c                         101
```

<210> SEQ ID NO 9
<211> LENGTH: 135
<212> TYPE: DNA
<213> ORGANISM: Homo sapiens

<400> SEQUENCE: 9

```
gcatgatttt aaggactggt tgtttatgag ccaatcagag gtgttgaata aacacctccc       60
tactaggtca aggtagaaag gggagggcaa atattggaaa aaaaaacat gatgagaagt      120 ctataaaaat tgtgt                                                     135
```

<210> SEQ ID NO 10
<211> LENGTH: 141
<212> TYPE: DNA
<213> ORGANISM: Homo sapiens

<400> SEQUENCE: 10

```
tgcgggaatc agcctttgaa acgatggcca acagcagcta ataataaacc agtaatttgg       60
gatagacgag tagcaagagg gcattggttg gtgggtcacc ctccttctca gaacacatta     120
taaaaacctt ccgtttccac a                                              141
```

<210> SEQ ID NO 11
<211> LENGTH: 74
<212> TYPE: DNA
<213> ORGANISM: Homo sapiens

<400> SEQUENCE: 11

```
tgccactcct agttcccatc ctatttaaat ctgcaagagg tttggttaat cattggcttt       60
gtcctgtgta gaca                                                       74
```

<210> SEQ ID NO 12
<211> LENGTH: 441
<212> TYPE: DNA

<213> ORGANISM: Homo sapiens

<400> SEQUENCE: 12

```
ttccttcccc cttccaagac cccctgaat cctatcaaaa gcacatcttc cattcattgc    60
ttcccggtgt cattatgaca agcggctaca aatcaatagc agagggaaag gcaggaccaa  120
cccgcactca ccaagtgata aagattcact ctcagccccg atttgctaat agcccataat  180
agcagccatt ggcgcccgc attaaataat acatttcact ccgcgtttat tatgggattt    240
ttaaaactcc tcaccaaatt ggattttctc gatggtctct aatttccaca tttatcattt  300
aaaattaaac tgctctgtgg aaagggggga tagagaagaa gaaggtagag agaggccaga  360
cagtactgta ttttttcctt tgactccccc ctttatgaaa acccataaat aatatcaggt  420
atcacagcta taagcagcag g                                             441
```

<210> SEQ ID NO 13
<211> LENGTH: 171
<212> TYPE: DNA
<213> ORGANISM: Homo sapiens

<400> SEQUENCE: 13

```
aggaggaact gctcaaaaca gacagaggct ctttgtttgc tttgcttctg tgtcaactgg    60
gcaacatttg gaaacaacaa atattggttc agaggcccac tgctttctta cccacctcct  120
gctggtcagc ttttccagct ttcctgcacg tacacacaag cgcagctatt t            171
```

<210> SEQ ID NO 14
<211> LENGTH: 170
<212> TYPE: DNA
<213> ORGANISM: Homo sapiens

<400> SEQUENCE: 14

```
cgatgctcta atctctctag acaaggttca tatttgtatg ggttacttat tctctctttg    60
ttgactaagt caataatcag aatcagcagg tttgcagtca gattggcagg ataagcagc   120
ctagctcagg agaagtgagt ataaaagccc caggctggga gcagccatca              170
```

<210> SEQ ID NO 15
<211> LENGTH: 48
<212> TYPE: DNA
<213> ORGANISM: artificial
<220> FEATURE:
<223> OTHER INFORMATION: Forward primer

<400> SEQUENCE: 15

```
aagcggccgc ggtaccgtct gtctgcacat ttcgtagagc gagtgttc                 48
```

<210> SEQ ID NO 16
<211> LENGTH: 36
<212> TYPE: DNA
<213> ORGANISM: artificial
<220> FEATURE:
<223> OTHER INFORMATION: Reverse primer

<400> SEQUENCE: 16

```
agcgctagcc aggagcttgt ggatctgtgt gacggc                              36
```

<210> SEQ ID NO 17
<211> LENGTH: 223
<212> TYPE: DNA
<213> ORGANISM: artificial
<220> FEATURE:
<223> OTHER INFORMATION: TTRmin sequence
```

```
<400> SEQUENCE: 17
gtctgtctgc acatttcgta gagcgagtgt tccgatactc taatctccct aggcaaggtt        60
catatttgtg taggttactt attctccttt tgttgactaa gtcaataatc agaatcagca       120
ggtttggagt cagcttggca gggatcagca gcctgggttg gaaggagggg gtataaaagc       180
cccttcacca ggagaagccg tcacacagat ccacaagctc ctg                         223

<210> SEQ ID NO 18
<211> LENGTH: 114
<212> TYPE: DNA
<213> ORGANISM: artificial
<220> FEATURE:
<223> OTHER INFORMATION: SEQ ID NO: 1 with restriction site

<400> SEQUENCE: 18
ggtaccggcg cgccggagtt gctggtgctt ccccaggctg agattgagt taatattaac         60 aggcccaagg cgatgtgggc ttgtgcaatc ataggcccgg ccacgcgtgg tacc             114

<210> SEQ ID NO 19
<211> LENGTH: 67
<212> TYPE: DNA
<213> ORGANISM: artificial
<220> FEATURE:
<223> OTHER INFORMATION: SEQ ID NO: 2 with restriction site

<400> SEQUENCE: 19
ggtaccggcg cgccatcgcc aggtcacctg aggagttaat gaatacatat ctcctacgcg        60
tggtacc                                                                  67

<210> SEQ ID NO 20
<211> LENGTH: 98
<212> TYPE: DNA
<213> ORGANISM: artificial
<220> FEATURE:
<223> OTHER INFORMATION: SEQ ID NO: 3 with restriction site

<400> SEQUENCE: 20
ggtaccggcg cgccgggggga ggctgctggt gaatattaac caaggtcacc ccagttatcg       60
gaggagcaaa caggggctaa gtccacacgc gtggtacc                                98

<210> SEQ ID NO 21
<211> LENGTH: 97
<212> TYPE: DNA
<213> ORGANISM: artificial
<220> FEATURE:
<223> OTHER INFORMATION: SEQ ID NO: 4 with restriction site

<400> SEQUENCE: 21
ggtaccggcg cgcctgaatg accttcagcc tgttcccgtc cctgatatgg gcaaacattg        60
caagcagcaa acagcaaaca catagacgcg tggtacc                                 97

<210> SEQ ID NO 22
<211> LENGTH: 199
<212> TYPE: DNA
<213> ORGANISM: artificial
<220> FEATURE:
<223> OTHER INFORMATION: SEQ ID NO: 5 with restriction site

<400> SEQUENCE: 22
ggtaccggcg cgccggcgta ttcttaagaa tagattaaat aatcataaaa agatctatac        60
```

```
ttaaaaattg aaaaatgctt aaatattaaa attcttctca taaaaaaata ctaatttaaa    120
aatgagcctg aaatgtttat ctatttattg cacagggttg catacataaa acgacacacc    180
ctcttgtacg cgtggtacc                                                 199
```

<210> SEQ ID NO 23
<211> LENGTH: 576
<212> TYPE: DNA
<213> ORGANISM: artificial
<220> FEATURE:
<223> OTHER INFORMATION: SEQ ID NO: 6 with restriction site

<400> SEQUENCE: 23

```
ggtaccggcg cgccagtttg gaacaagact atataccata tcctacagga agaataaaag    60
taaaggaaag gtgccatctc tactgaatag agagtcctaa caaaaaggct tcaaaaggac    120
tctgcatctt taataatata aaaaggctag gacacaaaca gcatcatcta aaatgccatt    180
agaaatactt cacatacaaa aaggtctaag taaagcagga ttttataaag tgatcaaaaa    240
agaaacacta aggggggaaaa atcttttaag attaaagagg ttttttcaaag gacaagttga    300 agtggctgta aaatttatga ggcagcatta aacttcagtt ctaagtaaca ataaattatt    360
caccataaaa acatacatgt gtcaaatatt ataagcctct taaactttttt aaaacaattt    420 cttgcagaac tgattagata tattaagtca agattagcag atactaactt tttcattagc    480
atactatgat cactcagagt aaaggaggaa atttagaaaa gaaataagac agaaccatca    540
atagtcgatt caccaccaaa tgtgacgcgt ggtacc                              576
```

<210> SEQ ID NO 24
<211> LENGTH: 119
<212> TYPE: DNA
<213> ORGANISM: artificial
<220> FEATURE:
<223> OTHER INFORMATION: SEQ ID NO: 7 with restriction site

<400> SEQUENCE: 24

```
ggtaccggcg cgcctaaaat gggcaaacat tgcaagcagc aaacagcaaa cacacagccc    60
tccctgcctg ctgaccttgg agctggggca gaggtcagag acctctcacg cgtggtacc    119
```

<210> SEQ ID NO 25
<211> LENGTH: 126
<212> TYPE: DNA
<213> ORGANISM: artificial
<220> FEATURE:
<223> OTHER INFORMATION: SEQ ID NO: 8 with restriction site

<400> SEQUENCE: 25

```
ggtaccggcg cgccagccaa tgaaatacaa agatgagtct agttaataat ctacaattat    60
tggttaaaga agtatattag tgctaatttc cctccgtttg tcctagcttt tctcacgcgt    120
ggtacc                                                              126
```

<210> SEQ ID NO 26
<211> LENGTH: 161
<212> TYPE: DNA
<213> ORGANISM: artificial
<220> FEATURE:
<223> OTHER INFORMATION: SEQ ID NO: 9 with restriction site

<400> SEQUENCE: 26

```
ggtaccggcg cgccgcatga ttttaaggac tggttgttta tgagccaatc agaggtgttg    60
aataaacacc tccctactag gtcaaggtag aaaggggagg gcaaatattg gaaaaaaaaa    120
```

-continued acatgatgag aagtctataa aaattgtgta cgcgtggtac c    161

<210> SEQ ID NO 27
<211> LENGTH: 166
<212> TYPE: DNA
<213> ORGANISM: artificial
<220> FEATURE:
<223> OTHER INFORMATION: SEQ ID NO: 10 with restriction site

<400> SEQUENCE: 27
ggtaccggcg cgcctgcggg aatcagcctt tgaaacgatg gccaacagca gctaataata    60
aaccagtaat ttgggataga cgagtagcaa gagggcattg gttggtgggt caccctcctt    120
ctcagaacac attataaaaa ccttccgttt ccacacgcgt ggtacc    166

<210> SEQ ID NO 28
<211> LENGTH: 99
<212> TYPE: DNA
<213> ORGANISM: artificial
<220> FEATURE:
<223> OTHER INFORMATION: SEQ ID NO: 11 with restriction site

<400> SEQUENCE: 28
ggtaccggcg cgcctgccac tcctagttcc catcctattt aaatctgcaa gaggtttggt    60
taatcattgg ctttgtcctg tgtagacacg cgtggtacc    99

<210> SEQ ID NO 29
<211> LENGTH: 467
<212> TYPE: DNA
<213> ORGANISM: artificial
<220> FEATURE:
<223> OTHER INFORMATION: SEQ ID NO: 12 with restriction site

<400> SEQUENCE: 29
ggtaccggcg cgccttcctt cccccttcca agacccccct gaatcctatc aaaagcacat    60
cttccattca ttgcttcccg gtgtcattat gacaagcggc tacaaatcaa tagcagaggg    120
aaaggcagga ccaacccgca ctcaccaagt gataaagatt cactctcagc ccgatttgc    180 taatagccca taatagcagc cattggcgcc ccgcattaaa taatacattt cactccgcgt    240
ttattatggg attttaaaa ctcctcacca aattggattt tctcgatggt ctctaatttc    300
cacatttatc atttaaaatt aaactgctct gtggaaaggg gggatagaga agaagaaggt    360
agagagaggc cagacagtac tgtatttttc cttttgactc cccccttat gaaaacccat    420 aaataatatc aggtatcaca gctataagca gcaggacgcg tggtacc    467

<210> SEQ ID NO 30
<211> LENGTH: 197
<212> TYPE: DNA
<213> ORGANISM: artificial
<220> FEATURE:
<223> OTHER INFORMATION: SEQ ID NO: 13 with restriction site

<400> SEQUENCE: 30
ggtaccggcg cgccaggagg aactgctcaa aacagacaga ggctctttgt ttgctttgct    60
tctgtgtcaa ctgggcaaca tttgaaaaca acaaatattg gttcagaggc ccactgcttt    120
cttacccacc tcctgctggt cagcttttcc agctttcctg cacgtacaca caagcgcagc    180
tatttacgcg tggtacc    197

<210> SEQ ID NO 31

```
<211> LENGTH: 194
<212> TYPE: DNA
<213> ORGANISM: artificial
<220> FEATURE:
<223> OTHER INFORMATION: SEQ ID NO: 14 with restriction site

<400> SEQUENCE: 31
ggtaccggcg cgccgatgct ctaatctctc tagacaaggt tcatatttgt atgggttact      60
tattctctct tgttgactaa gtcaataat cagaatcagc aggtttgcag tcagattggc     120
agggataagc agcctagctc aggagaagtg agtataaaag ccccaggctg ggagcagcca    180
tcacgcgtgg tacc                                                      194

<210> SEQ ID NO 32
<211> LENGTH: 22
<212> TYPE: DNA
<213> ORGANISM: Artificial Sequence
<220> FEATURE:
<223> OTHER INFORMATION: Forward primer

<400> SEQUENCE: 32
agggatatcg acttgcagaa aa                                              22

<210> SEQ ID NO 33
<211> LENGTH: 27
<212> TYPE: DNA
<213> ORGANISM: Artificial Sequence
<220> FEATURE:
<223> OTHER INFORMATION: Probe

<400> SEQUENCE: 33
agtcctgtga accagcagtg ccatttc                                         27

<210> SEQ ID NO 34
<211> LENGTH: 25
<212> TYPE: DNA
<213> ORGANISM: Artificial Sequence
<220> FEATURE:
<223> OTHER INFORMATION: Reverse primer

<400> SEQUENCE: 34
gtgagcttag aagtttgtga aacag                                           25

<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35
gccttctagt tgccagccat                                                 20

<210> SEQ ID NO 36
<211> LENGTH: 20
<212> TYPE: DNA
<213> ORGANISM: Artificial Sequence
<220> FEATURE:
<223> OTHER INFORMATION: Probe

<400> SEQUENCE: 36
tgtttgcccc tccccgtgc                                                  20

<210> SEQ ID NO 37
<211> LENGTH: 19
```

```
<212> TYPE: DNA
<213> ORGANISM: Artificial Sequence
<220> FEATURE:
<223> OTHER INFORMATION: Reverse primer

<400> SEQUENCE: 37
ggcaccttcc agggtcaag                                                19

<210> SEQ ID NO 38
<211> LENGTH: 20
<212> TYPE: DNA
<213> ORGANISM: Artificial Sequence
<220> FEATURE:
<223> OTHER INFORMATION: Forward primer

<400> SEQUENCE: 38
tgtgtccgtc gtggatctga                                               20

<210> SEQ ID NO 39
<211> LENGTH: 29
<212> TYPE: DNA
<213> ORGANISM: Artificial Sequence
<220> FEATURE:
<223> OTHER INFORMATION: Probe

<400> SEQUENCE: 39
cctggagaaa cctgccaagt atgatgaca                                     29

<210> SEQ ID NO 40
<211> LENGTH: 21
<212> TYPE: DNA
<213> ORGANISM: Artificial Sequence
<220> FEATURE:
<223> OTHER INFORMATION: Reverse primer

<400> SEQUENCE: 40
cctgcttcac caccttcttg a                                             21
```